(12) United States Patent
Nomoto et al.

(10) Patent No.: US 8,460,639 B2
(45) Date of Patent: Jun. 11, 2013

(54) PROBE FOR A HAIR CELL, AND LABELLING METHOD FOR A HAIR CELL USING THE PROBE FOR A HAIR CELL

(75) Inventors: Tsuyoshi Nomoto, Tokyo (JP); Takeshi Miyazaki, Yokohama (JP); Kohei Watanabe, Yokohama (JP); Taichi Shintou, Saitama (JP); Kaoru Takahashi, Saitama (JP); Toshio Tanaka, Tsu (JP); Yuhei Nishimura, Tsu (JP); Yasuhito Shimada, Nagoya (JP); Norihiro Nishimura, Tsu (JP)

(73) Assignee: Canon Kabushiki Kaisha, Tokyo (JP)

( * ) Notice: Subject to any disclaimer, the term of this patent is extended or adjusted under 35 U.S.C. 154(b) by 483 days.

(21) Appl. No.: 12/644,472

(22) Filed: Dec. 22, 2009

(65) Prior Publication Data

US 2010/0166663 A1    Jul. 1, 2010

(30) Foreign Application Priority Data

Dec. 25, 2008   (JP) ................................ 2008-330979

(51) Int. Cl.
*A61B 5/00*      (2006.01)

(52) U.S. Cl.
USPC .......................................................... 424/9.6

(58) Field of Classification Search
None
See application file for complete search history.

(56) References Cited

U.S. PATENT DOCUMENTS

| | | | |
|---|---|---|---|
| 5,350,580 A | 9/1994 | Muchow et al. | 424/437 |
| 5,476,446 A | 12/1995 | Arenburg | 604/21 |
| 2006/0188445 A1 | 8/2006 | Ou et al. | 424/9.2 |

FOREIGN PATENT DOCUMENTS

| | | |
|---|---|---|
| AU | 737695 | 3/1999 |
| EP | 1 813 263 A1 | 8/2007 |
| EP | 2157088 A1 | 2/2010 |
| JP | 2005082678 A * | 3/2005 |
| JP | 2008-094897 | 4/2008 |
| WO | 99/007334 | 2/1999 |
| WO | 00/76466 A1 | 12/2000 |
| WO | 2008/127139 A1 | 10/2008 |

OTHER PUBLICATIONS

Krieg R, Eitner A, Günther W, Schürer C, Lindenau J, Halbhuber KJ. N,N-Dialkylaminostyryl dyes: specific and highly fluorescent substrates of peroxidase and their application in histochemistry. 2008 J. Mol. Histol. 39: 169-191. Published online, Nov. 29, 2007.*
'Monomeric cyanine nucleic acid stains' product manual. Feb. 2, 2011 version. Invitrogen. 3 pages. Available online at http://tools.invitrogen.com/content/sfs/manuals/mp03602.pdf. Accessed Jun. 4, 2012.*
C.A. Bertolino et al., "Solvent Effect on Indocyanine Dyes: A Computational Approach", *Chemical Physics*, vol. 330, pp. 52-59 (2006).
Official Action dated Apr. 1, 2011 in European Application No. 09 015 904.7.
European Search Report dated Aug. 5, 2010 in European Application No. 09015904.7.
Swan, et al., "Inner ear drug delivery for auditory applications", Advanced Drug Delivery Reviews, vol. 60, 2008, pp. 1583-1599.
Hu, "Delayed mitochondrial dysfunction in apoptotic hair cells in chinchilla cochleae following exposure to impulse noise", Apoptosis, vol. 12, 2007, pp. 1025-1036.
C Ton et al., "The Use of Zebrafish for Assessing Ototoxic and Otoprotective Agents", in *Hearing Research*, 208, pp. 79-88, 2005.
S Nishikawa et al., "Internalization of Styryl Dye FM1-43 in the Hair Cells of Lateral Line Organs of *Xenopus* Larvae", in *The Journal of Histochemistry and Cytochemistry*, 44(7), pp. 733-741, 1996.
European Search Report dated Feb. 15, 2012 in European Application No. 11008027.2.
Yamashita, et al., "Post-Exposure Treatment Attenuates Noise-Induced Hearing Loss", Neuroscience, vol. 134, No. 2, 2005, pp. 633-642.
European Office Action dated Dec. 27, 2011 in European Application No. 09 015 904.7.
Seligmann, et al., "Drug-Induced Tinnitus and Other Hearing Disorders", Drug Safety, vol. 14, No. 3, 1996, pp. 198-212.

* cited by examiner

*Primary Examiner* — Michael G Hartley
*Assistant Examiner* — Jennifer Lamberski
(74) *Attorney, Agent, or Firm* — Fitzpatrick, Cella, Harper & Scinto

(57) ABSTRACT

Provided are a novel probe for a hair cell for clearly identifying various conditions of a hair cell, and a labelling method for a hair cell using the probe for a hair cell, more particularly, a probe for a hair cell containing, as an active agent, a staining compound represented by the general formula (I)

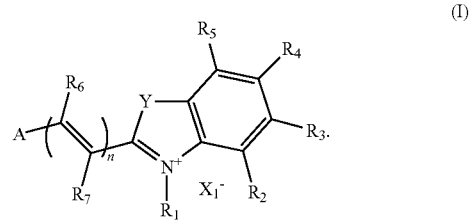

(I)

9 Claims, 2 Drawing Sheets

PROBE FOR A HAIR CELL, AND LABELLING METHOD FOR A HAIR CELL USING THE PROBE FOR A HAIR CELL

BACKGROUND OF THE INVENTION

1. Field of the Invention

The present invention relates to a probe for a hair cell, and a labelling method for a hair cell using the probe for a hair cell.

2. Description of the Related Art

In a human, a hair cell exists in the cochlea which is an auditory receptor, and in the semicircular canals and vestibular organs both of which are vestibular sensory receptors. The hair cell is covered with special cilia. The cilia perceive the movement of lymph generated depending on a sound, a motion, and a posture, and then cause an electrical change.

The abnormality of the hair cell is said to relate to factors of disorders such as peripheral sensorineural auditory impairment (hearing loss), tinnitus, and vertigo. The hair cell itself is active in metabolism, and in particular, is fragile to and easily damaged by the expose to noise and chemicals. A list of medicaments and chemical substances which may have hair cell toxicity has been reported. The list includes, for example, an antibiotic such as an aminoglycoside antibiotic, an anti-inflammatory drug, a diuretic drug, an antimalarial drug, an antitumor drug, and a topical agent (Drug Safety: an International Journal of Medical Toxicology and Drug Experience, 14(3), pp. 198-212, 1996).

However, thus far, there is no standardized screening method for auditory toxicity in a drug development stage, and further, many of already approved medicaments remain unknown for their auditory toxicity.

For means for evaluating the auditory toxicity of a chemical substance, for example, means for evaluating the life and death of a hair cell of Zebrafish with a fluorescent dye such as 2-(4-(dimethylamino)styryl)-N-ethylpyridinium iodide (DASPEI) is reported (Hearing Research, 208, pp. 79-88, 2005). Further, FM1-43 is known as a hair cell staining dyestuff (The Journal of Histochemistry and Cytochemistry, 44(7), pp. 733-741, 1996).

For an expression mechanism of the auditory toxicity with a chemical substance, various modes may be estimated. That is, there is a diversity in the type of injuries on a' hair cell function due to a difference in a target biomolecule (such as a protein, an enzyme, a nucleic acid, and a gene) of a chemical substance. Accordingly, it is important to identify various conditions of a hair cell (for example, loss of a specific cell function as well as life and death of a cell) depending on the diversity in the type of injuries. Therefore, there is a demand for hair cell staining agents having various chemical structures.

However, known compounds for staining a hair cell are only the two kinds (DASPEI and FM1-43) exemplified above. Those compounds are close to each other in terms of the excitation wavelength and fluorescence emission wavelength, and they do not sufficiently contribute to enlargement of variations for selection of staining technologies depending on the above mentioned diversity in modes and on the purposes such as multiple staining.

SUMMARY OF THE INVENTION

It is an object of the present invention to provide a novel probe for a hair cell for clearly identifying various conditions of a hair cell. Further, it is another object of the present invention to provide an evaluation method for an auditory function such as evaluation of the auditory toxicity of a chemical substance and imaging of the hair cell, by labeling a hair cell specifically using the novel probe for a hair cell.

It is still another object of the present invention to provide a diagnostic composition for an auditory function for evaluating a condition of a hair cell in a living body.

It is yet still another object of the present invention to provide a screening method for one of a therapeutic drug and a preventive drug for hearing loss.

It is even yet still another object of the present invention to provide an evaluation method for one of a therapeutic drug and a preventive drug for hearing loss.

The probe for a hair cell according to the present invention contains, as an active agent, at least one kind selected from staining compounds represented by one of the general formulae (I) and (II).

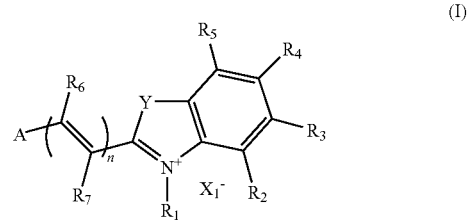

(I)

where; $R_1$ represents one of a hydrogen atom, an alkyl group, and an aryl group, $R_2$ to $R_5$ each independently represent one of a hydrogen atom, an alkyl group, an aryl group, an alkoxy group, a carboxylic acid group, a sulfonic acid group, a heterocyclic group, an amino group, and a halogen atom, one of $R_2$ and $R_3$, $R_3$ and $R_4$, and $R_4$ and $R_5$ may be bonded to each other to form a ring, $R_6$ represents one of a hydrogen atom and an alkyl group, and $R_7$ represents one of a hydrogen atom, an alkyl group, a carboxylic acid group, and a cyano group, $X_1^-$ represents an anionic group, Y represents one of a sulfur atom, an oxygen atom, —N($R_8$)—, and —C($R_9$)($R_{10}$)—, $R_8$ to $R_{10}$ each independently represent one of a hydrogen atom, an alkyl group, and an aryl group, and $R_9$ and $R_{10}$ may be bonded to each other to form a ring, A represents one of an aryl group and an alkenyl group, and n represents an integer of 1 to 3, and when n represents 1, A and $R_6$ may be condensed with each other to form a ring, and

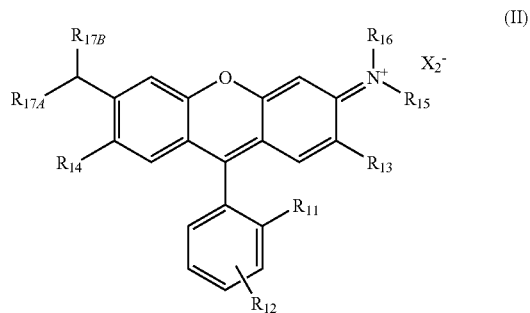

(II)

where; $R_{11}$ and $R_{12}$ each independently represent one of a carboxylic acid group, a carboxylic acid ester group, a carboxylic acid amide group, a sulfonic acid group, a sulfonic acid ester group, a sulfonic acid amide group, a carboxylic acid salt, and a sulfonic acid salt, $R_{13}$ and $R_{14}$ each independently represent one of a hydrogen atom, an alkyl group, and an aryl group, and $R_{15}$, $R_{16}$, $R_{17A}$, and $R_{17B}$ each independently represent one of a hydrogen atom, an alkyl group, an aryl group, and a heterocyclic group, and
$X_2^-$ represents an anionic group.

Further, an imaging method for a hair cell according to the present invention includes; bringing a biological specimen into contact with the probe for a hair cell of the present invention, and observing fluorescence derived from the probe for a hair cell by irradiating the biological specimen with excitation light.

An evaluation method for auditory toxicity of a chemical substance according to the present invention includes; administering the chemical substance to an organism, bringing the organism into contact with the probe for a hair cell of the present invention, and observing fluorescence derived from the probe for a hair cell by irradiating the organism with excitation light.

A diagnostic composition for an auditory function according to the present invention includes, as an active agent, the probe for a hair cell of the present invention.

A screening method for one of a therapeutic drug and a preventive drug for hearing loss according to the present invention includes; administering a test substance to a hearing loss model animal, administering the diagnostic composition for an auditory function of the present invention to the model animal, and examining a staining condition of the diagnostic composition for an auditory function for a hair cell of the model animal.

An evaluation method for one of a therapeutic drug and a preventive drug for hearing loss according to the present invention includes; administering a test substance to a hearing loss model animal, administering the diagnostic composition for an auditory function of the present invention to the model animal, and examining a staining condition of the diagnostic composition for an auditory function for a hair cell of the model animal.

According to the present invention, there is provided a novel application of a compound different in wavelength property from a conventional hair cell staining agent. Further, a compound group used for the probe for a hair cell according to the present invention is rich in diversity in combinations of the excitation wavelength/fluorescence emission wavelength, and can clearly visualize a neuromast present in lateral line organs.

Further features of the present invention will become apparent from the following description of exemplary embodiments with reference to the attached drawings.

DESCRIPTION OF THE EMBODIMENTS

Figure 1:
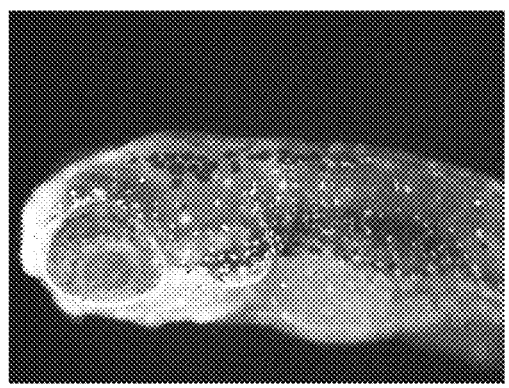
FIG. 1 shows a fluorescence observation image of a Zebrafish neuromast observed in Example 10.

Hereinafter, the present invention is described in more detail.

The inventors of the present invention have found that a probe for a hair cell containing, as an active agent, at least one kind selected from staining compounds represented by one of the general formulae (I) and (II) is a novel probe for a hair cell that labels a hair cell with high sensitivity, and enables more precise diagnosis and drug screening. Thus, the present invention has been completed.

It should be noted that the phrase "labelling of a hair cell" as used herein means that the above-mentioned active agent is retained inside, on a surface of, or in the periphery of a hair cell, resulting in such a condition that at least one of the shape, location, and function of the hair cell can be detected. For example, a method of capturing a fluorescence image and a staining image using an image capturing unit as described below, and a visual observation method are employed for the detection.

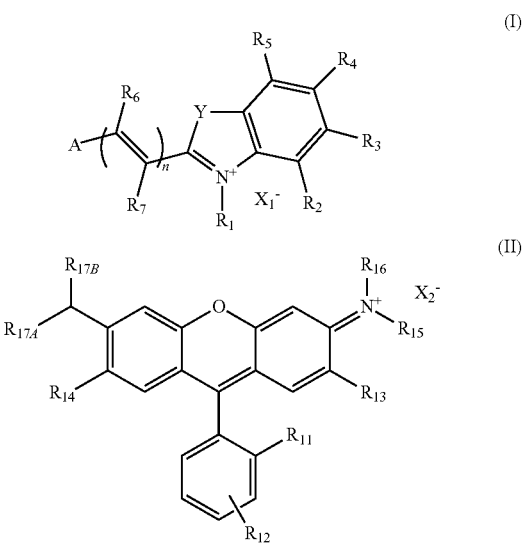

In the general formula (I); $R_1$ represents one of a hydrogen atom, an alkyl group, and an aryl group, $R_2$ to $R_5$ each independently represent one of a hydrogen atom, an alkyl group, an aryl group, an alkoxy group, a carboxylic acid group, a sulfonic acid group, a heterocyclic group, an amino group, and a halogen atom, one of $R_2$ and $R_3$, $R_3$ and $R_4$, and $R_4$ and $R_5$ may be bonded to each other to form a ring, $R_6$ represents one of a hydrogen atom and an alkyl group, $R_7$ represents one of a hydrogen atom, an alkyl group, a carboxylic acid group, and a cyano group, $X_1^-$ represents an anionic group, Y represents one of a sulfur atom, an oxygen atom, —N($R_8$)—, and —C($R_9$)($R_{10}$)—, $R_8$ to $R_{10}$ each independently represent one of a hydrogen atom, an alkyl group, and an aryl group, $R_9$ and $R_{10}$ may be bonded to each other to form a ring, A represents one of an aryl group and an alkenyl group; and n represents an integer of 1 to 3, and when n represents 1, A and $R_6$ may be condensed together to form a ring.

In the general formula (II); $R_{11}$ and $R_{12}$ each represent one of a carboxylic acid group, a carboxylic acid ester group, a carboxylic acid amide group, a sulfonic acid group, a sulfonic acid ester group, a sulfonic acid amide group, a carboxylic acid salt, and a sulfonic acid salt, $R_{13}$ and $R_{14}$ each independently represent one of a hydrogen atom, an alkyl group, and an aryl group, $R_{15}$, $R_{16}$, $R_{17A}$, and $R_{17B}$ each independently represent one of a hydrogen atom, an alkyl group, an aryl group, and a heterocyclic group, and $X_2^-$ represents an anionic group.

The alkyl group represented by $R_1$ in the general formula (I) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

$R_1$ may further have a substituent and the substituent is not particularly limited as long as the storage stability of the staining compound is not significantly inhibited. Examples thereof include; alkyl groups such as a methyl group, an ethyl group, an n-propyl group, an isopropyl group, an n-butyl group, an isobutyl group, a sec-butyl group, and a tert-butyl group, aryl groups such as a phenyl group and a naphthyl group, alkoxy groups such as a methoxy group, an ethoxy group, and a butoxy group, aryloxy groups such as a phenoxy group and a naphthyloxy group, alkylsulfanyl groups such as a thiomethyl group, a thioethyl group, a thiopropyl group, a thiobutyl group, and a thiophenyl group, monosubstituted amino groups such as a methylamino group and a butylamino group, disubstituted amino groups such as a dimethylamino group, an N-ethyl-N-phenylamino group, and a diphenylamino group, acyl groups such as an acetyl group, a benzoyl group, a carboxylic acid group, a carboxylic acid ester group, and a carbamoyl group, sulfonyl groups such as a sulfonic acid group, a sulfonic acid ester group, and a sulfamoyl group, heterocyclic groups such as a pyridyl group, a triazinyl group, and a benzothiazolyl group, a nitro group; halogen atoms such as a fluorine atom, a chlorine atom, a bromine atom, and an iodine atom; a polyethylene glycol group, and salts such as a quarternary ammonium salt, a carboxylic acid salt, and a sulfonic acid salt. Of those substituents, it is preferred that $R_1$ have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

The aryl group represented by $R_1$ is not particularly limited and examples thereof include 6 to 14-membered monocyclic and polycyclic aryl groups such as a phenyl group, a naphthyl group, a phenanthryl group, and an anthracenyl group.

A preferred example of $R_1$ includes an alkyl group, and more preferred is an alkyl group having a substituent such as a carboxylic acid group, a sulfonic acid group, a polyethylene glycol group, a carboxylic acid salt, and a sulfonic acid salt because the alkyl group increases the water solubility of the compound and also increases the fluorescence intensity. The alkyl group represented by each of $R_2$ to $R_5$ in the general formula (I) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_2$ to $R_5$ is not particularly limited and examples thereof include 6 to 14-membered monocyclic and polycyclic aryl groups such as a phenyl group, a naphthyl group, a phenanthryl group, and an anthracenyl group.

The alkoxy group represented by each of $R_2$ to $R_5$ is not particularly limited and examples thereof include alkoxy groups having 1 to 20 carbon atoms such as a methoxy group, an ethoxy group, a propoxy group, a butoxy group, a pentyloxy group, a decyloxy group, a hexyloxy group, a heptyloxy group, an octyloxy group, a nonyloxy group, a decyloxy group, a dodecyloxy group, and an octadecyloxy group.

The heterocyclic group represented by each of $R_2$ to $R_5$ is not particularly limited and examples thereof include 4 to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

The amino group represented by each of $R_2$ to $R_5$ is not particularly limited and examples thereof include; an unsubstituted amino group, monosubstituted amino groups such as an N-methylamino group, an N-butylamino group, an N-hexylamino group, an N-tetradecylamino group, an N-phenylamino group, and an N-naphthylamino group, disubstituted amino groups such as an N,N-dimethylamino group, an N,N-diethylamino group, an N,N-diphenylamino group, and an N,N-methylpropylamino group, carbonylamino groups such as an acetylamino group, an ethylcarbonylamino group, a tert-butylcarbonylamino group, a benzoylamino group, a naphthoylamino group, and a methoxycarbonylamino group, and sulfonylamino groups such as a methylsulfonylamino group, an ethylsulfonylamino, group, a tert-butylsulfonylamino group, and an isopropoxysulfonylamino group.

Examples of the halogen atom represented by each of $R_2$ to $R_5$ include a fluorine atom, a chlorine atom, a bromine atom, and an iodine atom.

$R_2$ to $R_5$ each preferably represent one of a hydrogen atom, a carboxylic acid group, a sulfonic acid group, an amino group, and a halogen atom, and more preferably represent a hydrogen atom and a sulfonic acid group, each of which improves the water solubility of the compound.

The ring which is formed by one of $R_2$ and $R_3$, $R_3$ and $R_4$, and $R_4$ and $R_5$ bonded to each other is not particularly limited and examples thereof include; aromatic rings having 3 to 10 carbon atoms such as a benzene ring and a naphthalene ring, saturated rings such as a cyclooctane ring, a cycloheptane ring, a cyclohexane ring, a cyclopentane ring, and a cyclobutane ring, partially saturated rings such as a cyclopentene ring and a cyclohexene ring, and heterocycles such as a pyridine ring and a pyrimidine ring. Further, the ring may have a substituent and the substituent is not particularly limited as long as the storage stability of the staining compound is not significantly inhibited. Examples thereof include alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quarternary ammonium salt, a carboxylic acid salt, and a sulfonic acid salt.

The ring which is formed by one of $R_2$ and $R_3$, $R_3$ and $R_4$, and $R_4$ and $R_5$ bonded to each other is preferably a benzene ring, because the storage stability of the compound is improved.

The alkyl group represented by each of $R_6$ and $R_7$ in the general formula (I) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

$R_6$ preferably represents one of a hydrogen atom, a methyl group, an ethyl group, a propyl group, and a butyl group, and more preferably represents, in terms of stability of the compound, one of a hydrogen atom, a methyl group, and an ethyl group.

$R_7$ preferably represents one of a hydrogen atom and a cyano group, and more preferably represents a hydrogen atom.

$X_1^-$ in the general formula (I) represents an anionic group. Here, the anionic group is not particularly limited and examples thereof include: halogen ions such as a fluoride ion, a chloride ion, a bromide ion, and an iodide ion; inorganic acid ions such as a sulfuric acid ion, a phosphoric acid ion, a nitric acid ion, a tetrafluoroboric acid ion, and a hexafluorophosphoric acid ion; Lewis acid-containing ions such as a tetrachloroaluminum ion; and organic acid ions such as an acetic acid ion, a lactic acid ion, a methanesulfonic acid ion, a benzenesulfonic acid ion, a p-toluenesulfonic acid ion, a trifluoroacetic acid ion, a trifluoromethanesulfonic acid ion, and a tetraphenylboric acid ion.

The anionic group represented by $X_1^-$ is preferably one of a chloride ion, a bromide ion, an iodide ion, a sulfuric acid ion, a nitric acid ion, and a methanesulfonic acid ion, and more preferably, in terms of ease of synthesis of the compound, one of a bromide ion and an iodide ion.

Y in the general formula (I) represents one of a sulfur atom, an oxygen atom, —N($R_8$)—, and —C($R_9$)($R_{10}$)—.

In Y, the alkyl group represented by each of $R_8$ to $R_{10}$ is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

In Y, the aryl group represented by each of $R_8$ to $R_{10}$ is not particularly limited and examples thereof include 6 to 14-membered monocyclic and polycyclic aryl groups such as a phenyl group, a naphthyl group, a phenanthryl group, and an anthracenyl group.

Y preferably represents, in terms of storage stability of the compound, one of an oxygen atom, a sulfur atom, and —C(CH$_3$)(CH$_3$)—.

The aryl group represented by A in the general formula (I) is not particularly limited and examples thereof include 6 to 14-membered monocyclic and polycyclic aryl groups such as a phenyl group, a naphthyl group, a phenanthryl group, an indolyl group, and an anthracenyl group. Further, the ring may have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quarternary ammonium salt, a carboxylic acid salt, and a sulfonic acid salt. Of those substituents, it is preferred that the ring have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

The aryl group represented by A is preferably a compound represented by the following general formula (IV).

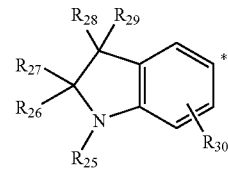

(IV)

In the general formula (IV): $R_{25}$ represents one of a hydrogen atom, an alkyl group, an aralkyl group, an alkenyl group, an aryl group, a heterocyclic group, and an acyl group; $R_{26}$ to $R_{29}$ each independently represent one of a hydrogen atom, an alkyl group, an aryl group, a carboxylic acid group, a carboxylic acid ester group, and an acyl group, and $R_{26}$ and $R_{28}$ may be bonded to each other to form a ring; and $R_{30}$ represents one of a hydrogen atom, an alkyl group, an alkoxy group, and a halogen atom.

The alkyl group represented by $R_{25}$ in the general formula (IV) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aralkyl group represented by $R_{25}$ is not particularly limited and examples thereof include a benzyl group and a phenethyl group.

The alkenyl group represented by $R_{25}$ is not particularly limited and examples thereof include alkenyl groups having 2 to 20 carbon atoms such as a vinyl group, a 2,2-diphenylvinyl group, a 3-butenyl group, and a cyclohexenyl group.

The aryl group represented by $R_{25}$ is not particularly limited and examples thereof include 6 to 14-membered monocyclic and polycyclic aryl groups such as a phenyl group, a naphthyl group, a phenanthryl group, and an anthracenyl group.

The heterocyclic group represented by $R_{25}$ is not particularly limited and examples thereof include 4 to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

$R_{25}$ may further have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quarternary ammonium salt, a carboxylic acid salt, and a sulfonic acid salt. Of those substituents, it is preferred that $R_{25}$ have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

$R_{25}$ may be independently and arbitrarily selected from the substituents exemplified above, and because the fluorescence intensity is large, preferred examples include an aralkyl group, an alkenyl group, and an aryl group. Specifically, a phenyl group, a bromophenyl group, a benzyl group, a bromobenzyl group, a methylthiophenyl group, a methoxyphenyl group, a methoxynaphthyl group, a benzylphenyl group, a 2,2-diphenylvinyl group, and a 2,2-diphenylvinylphenyl group are preferred. More preferred are a phenyl group, a bromophenyl group, a benzyl group, a methylthiophenyl group, a methoxyphenyl group, and a methoxynaphthyl group. In particular, a methylthiophenyl group is preferred because there is a tendency that a Stokes' shift becomes remarkable large.

The alkyl group represented by each of $R_{26}$ to $R_{29}$ in the general formula (IV) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_{26}$ to $R_{29}$ is not particularly limited and examples thereof include 6 to 14-membered monocyclic and polycyclic aryl groups such as a phenyl group, a naphthyl group, a phenanthryl group, and an anthracenyl group.

The carboxylic acid ester group represented by each of $R_{26}$ to $R_{29}$ is not particularly limited and examples thereof include a carboxylic acid methyl ester group, a carboxylic acid ethyl ester group, a carboxylic acid propyl ester group, and a carboxylic acid butyl ester group.

The acyl group represented by each of $R_{26}$ to $R_{29}$ is not particularly limited and examples thereof include an acetyl group, a propionyl group, a butyryl group, a pentanoyl group, a benzoyl group, a 1-naphthoyl group, and a 2-naphthoyl group.

Each of $R_{26}$ to $R_{29}$ may further have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quarternary ammonium salt, a carboxylic acid salt, and a sulfonic acid salt. Of those substituents, it is preferred that each of $R_{26}$ to $R_{29}$ have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto. The ring which is formed by $R_{26}$ and $R_{28}$ bonded to each other is not particularly limited and examples thereof include: saturated aliphatic rings such as a cyclooctane ring, a cycloheptane ring, a cyclohexane ring, a cyclopentane ring, and a cyclobutane ring; and partially saturated aliphatic rings such as a cyclopentene ring and a cyclohexene ring. Further, the ring may have a substituent and the substituent is not particularly limited as long as the storage stability of the staining compound is not significantly inhibited. Examples thereof include alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quarternary ammonium salt, a carboxylic acid salt, and a sulfonic acid salt. Of those substituents, it is preferred that the ring have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

It is preferred that $R_{26}$ to $R_{29}$ each independently represent one of a hydrogen atom, an alkyl group, and an aryl group, and $R_{26}$ and $R_{28}$ be bonded to each other to form a ring. It is more preferred that $R_{26}$ and $R_{28}$ be bonded to each other to form a ring, which is a stable chemical structure. Specific examples thereof include a cyclooctane ring, a cycloheptane ring, a cyclohexane ring, a cyclopentane ring, and a cyclobutane ring. In terms of storage stability, a cyclopentane ring is more preferred.

The alkyl group represented by $R_{30}$ in the general formula (IV) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The alkoxy group represented by $R_{30}$ is not particularly limited and examples thereof include alkoxy groups having 1 to 20 carbon atoms such as a methoxy group, an ethoxy group, a propoxy group, a butoxy group, a pentyloxy group, a hexyloxy group, a heptyloxy group, an octyloxy group, a nonyloxy group, a decyloxy group, a dodecyloxy group, and an octadecyloxy group.

Examples of the halogen atom represented by $R_{30}$ include a fluorine atom, a chlorine atom, a bromine atom, and an iodine atom.

$R_{30}$ preferably represents one of a hydrogen atom, a halogen atom, and an alkoxy group, and more preferably represents one of a hydrogen atom and a halogen atom.

The alkenyl group represented by A is preferably a compound represented by the following general formula (III).

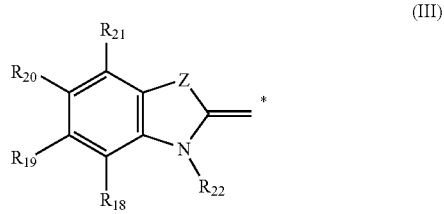

(III)

In the general formula (III): $R_{18}$ to $R_{21}$ each independently represent one of a hydrogen atom, an alkyl group, an aryl group, an alkoxy group, a carboxylic acid group, a sulfonic acid group, a heterocyclic group, an amino group, and a halogen atom; one of $R_{18}$ and $R_{19}$, $R_{19}$ and $R_{20}$, and $R_{20}$ and $R_{21}$ may be bonded to each other to form a ring; $R_{22}$ represents one of a hydrogen atom, an alkyl group, and an aryl group; Z represents one of a sulfur atom, an oxygen atom, and —$C(R_{23})(R_{24})$—; $R_{23}$ and $R_{24}$ each represent one of a hydrogen atom, an alkyl group, and an aryl group; and $R_{23}$ and $R_{24}$ may be bonded to each other to form a ring.

The alkyl group represented by each of $R_{18}$ to $R_{21}$ in the general formula (III) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_{18}$ to $R_{21}$ is not particularly limited and examples thereof include 6 to 14-membered monocyclic and polycyclic aryl groups such as a phenyl group, a naphthyl group, a phenanthryl group, and an anthracenyl group.

The alkoxy group represented by each of $R_{18}$ to $R_{21}$ is not particularly limited and examples thereof include alkoxy groups having 1 to 20 carbon atoms such as a methoxy group, an ethoxy group, a propoxy group, a butoxy group, a pentyloxy group, a decyloxy group, a hexyloxy group, a heptyloxy group, an octyloxy group, a nonyloxy group, a decyloxy group, a dodecyloxy group, and an octadecyloxy group.

The heterocyclic group represented by each of $R_{18}$ to $R_{21}$ is not particularly limited and examples thereof include 4 to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

The amino group represented by each of $R_{18}$ to $R_{21}$ is not particularly limited and examples thereof include: an unsubstituted amino group; monosubstituted amino groups such as an N-methylamino group, an N-butylamino group, an N-hexylamino group, an N-tetradecylamino group, an N-phenylamino group, and an N-naphthylamino group; disubstituted amino groups such as an N,N-dimethylamino group, an N,N-diethylamino group, an N,N-diphenylamino group, and an N,N-methylpropylamino group; carbonylamino groups such as an acetylamino group, an ethylcarbonylamino group, a tert-butylcarbonylamino group, a benzoylamino group, a naphthoylamino group, and a methoxycarbonylamino group; and sulfonylamino groups such as a methylsulfonylamino group, an ethylsulfonylamino group, a tert-butylsulfonylamino group, and an iso-propoxysulfonylamino group.

Examples of the halogen atom represented by each of $R_{18}$ to $R_{21}$ include a fluorine atom, a chlorine atom, a bromine atom, and an iodine atom.

$R_{18}$ to $R_{21}$ each preferably represent one of a hydrogen atom, a carboxylic acid group, a sulfonic acid group, an amino group, and a halogen atom, and more preferably represent one of a hydrogen atom and a sulfonic acid group because the water solubility of the compound is improved.

The ring which is formed by one of $R_{18}$ and $R_{19}$, $R_{19}$ and $R_{20}$, and $R_{20}$ and $R_{21}$ bonded to each other is not particularly limited and examples thereof include: aromatic rings having 3 to 10 carbon atoms such as a benzene ring and a naphthalene ring; saturated rings such as a cyclooctane ring, a cycloheptane ring, a cyclohexane ring, a cyclopentane ring, and a cyclobutane ring; partially saturated rings such as a cyclopentene ring and a cyclohexene ring; and heterocycles such as a pyridine ring and a pyrimidine ring. Further, the ring may have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quarternary ammonium salt, a carboxylic acid salt, and a sulfonic acid salt. Of those substituents, it is preferred that the ring have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

The ring which is formed by one of $R_{18}$ and $R_{19}$, $R_{19}$ and $R_{20}$, and $R_{20}$ and $R_{21}$ bonded to each other is preferably a benzene ring, because the storage stability of the compound is improved.

The alkyl group represented by $R_{22}$ in the general formula (III) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

$R_{22}$ may further have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group; a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quarternary ammonium salt, a carboxylic acid salt, and a sulfonic acid salt. Of those substituents, it is preferred that $R_{22}$ have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

The aryl group represented by $R_{22}$ is not particularly limited and examples thereof include 6 to 14-membered monocyclic and polycyclic aryl groups such as a phenyl group, a naphthyl group, a phenanthryl group, and an anthracenyl group.

$R_{22}$ preferably represents an alkyl group, and the alkyl group further preferably has a substituent such as a carboxylic acid group, a sulfonic acid group, a polyethylene glycol group, a carboxylic acid salt, and a sulfonic acid salt, because those substituents improve the water solubility of the compound and also increase the fluorescence intensity. Specific examples thereof include a methyl group, an ethyl group, a propyl group, a butyl group, a pentyl group, a hexyl group, an octyl group, a nonyl group, an acetic acid group, a propanoic acid group, and an ethanesulfonic acid group.

The alkyl group represented by $R_{23}$ and $R_{24}$ in Z of the general formula (III) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

In Z, the aryl group represented by $R_{23}$ and $R_{24}$ is not particularly limited and examples thereof include 6 to 14-membered monocyclic and polycyclic aryl groups such as a phenyl group, a naphthyl group, a phenanthryl group, and an anthracenyl group.

In the general formula (III), Z particularly preferably represents, in terms of storage stability of the compound, one of an oxygen atom, a sulfur atom, and —C($CH_3$)($CH_3$)—.

In the general formula (I), n represents an integer of 1 to 3, and in terms of stability of the compound, n preferably represents 1. Further, when n represents 1, A and $R_6$ may be condensed together to form a ring.

Examples of the ring which is formed by A and $R_6$ condensed together include a squarylium ring and a thiazolidin-4-one ring.

Further, in the case of using light in a near-infrared area as excitation light, in the general formula (I), when A represents the general formula (III), n preferably represents one of 2 and 3.

Further, the compound represented by the general formula (I) preferably has at least one of a carboxylic acid group and a sulfonic acid group.

In the general formula (I), the ring formed by A and $R_6$ bonded to each other is not particularly limited and examples thereof include a 2,3-dihydroindene ring, an indene-1,3-dione ring, a 4-cyclopentene-1,3-dione ring, a fluorene ring, a cyclohexene ring, a hydroxycyclobutenone ring, a cyclohexanone ring, and a 5,5-dimethyl-1-cyclohexene ring.

In the general formula (II), the carboxylic acid ester group represented by each of $R_{11}$ and $R_{12}$ is not particularly limited and examples thereof include a carboxylic acid methyl ester group, a carboxylic acid ethyl ester group, a carboxylic acid propyl ester group, and a carboxylic acid butyl ester group.

The carboxylic acid amide group represented by each of $R_{11}$ and $R_{12}$ is not particularly limited and examples thereof include a carboxylic acid monomethyl amide group, a carboxylic acid monobutyl amide group, a carboxylic acid diethyl amide group, and a carboxylic acid 2-ethylhexyl group.

The sulfonic acid ester group represented by each of $R_{11}$ and $R_{12}$ is not particularly limited and examples thereof include a sulfonic acid methyl ester group, a sulfonic acid ethyl ester group, a sulfonic acid propionic acid ester group, and a sulfonic acid butyl ester group.

The sulfonic acid amide group represented by each of $R_{11}$ and $R_{12}$ is not particularly limited and examples thereof include a sulfonic acid monomethyl amide group, a sulfonic acid monobutyl amide group, a sulfonic acid diethyl amide group, and a sulfonic acid 2-ethylhexyl amide group.

The sulfonic acid salt and carboxylic acid salt represented by each of $R_{11}$ and $R_{12}$ are not particularly limited and examples thereof include: alkali metal salts such as a lithium salt, a sodium salt, and a potassium salt; and ammonium salts such as an ammonium salt, a methylammonium salt, a dimethylammonium salt, a trimethylammonium salt, a tetramethylammonium salt, an ethylammonium salt, a diethylammonium salt, a triethylammonium salt, and a tetraethylammonium salt, an n-propylammonium salt, an isopropylammonium salt, a diisopropylammonium salt, an n-butylammonium salt, a tetra-n-butylammonium salt, an isobutylammonium salt, a monoethanolammonium salt, a diethanolammonium salt, and a triethanolammonium salt.

$R_{11}$ and $R_{12}$ each preferably represent one of a sulfonic acid group, a carboxylic acid group, a sulfonic acid methyl ester group, a sulfonic acid ethyl ester group, a carboxylic acid methyl ester group, a carboxylic acid ethyl ester group, a carboxylic acid monobutyl amide group, a sulfonic acid monobutyl amide group, a sulfonic acid sodium salt, a sulfonic acid potassium salt, a sulfonic acid ammonium salt, a carboxylic acid sodium salt, a carboxylic acid potassium salt, and a carboxylic acid ammonium salt, and more preferably represent, in terms of improving the water solubility, one of a sulfonic acid group, a carboxylic acid group, a sulfonic acid sodium salt, and a carboxylic acid sodium salt.

The alkyl group represented by each of $R_{13}$ and $R_{14}$ in the general formula (II) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_{13}$ and $R_{14}$ is not particularly limited and examples thereof include 6 to 14-membered monocyclic and polycyclic aryl groups such as a phenyl group, a naphthyl group, a phenanthryl group, and an anthracenyl group.

$R_{13}$ and $R_{14}$ each preferably represent one of an alkyl group and a phenyl group, and more preferably one of a methyl group, an ethyl group, a propyl group, and a butyl group.

The alkyl group represented by each of $R_{15}$, $R_{16}$, $R_{17A}$, and $R_{17B}$ in the general formula (II) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_{15}$, $R_{16}$, $R_{17A}$, and $R_{17B}$ is not particularly limited and examples thereof include 6 to 14-membered monocyclic and polycyclic aryl groups such as a phenyl group, a naphthyl group, a phenanthryl group, and an anthracenyl group. Further, the ring may have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quarternary ammonium salt, a carboxylic acid salt, and a sulfonic acid salt.

The heterocyclic group represented by each of $R_{15}$, $R_{16}$, $R_{17A}$, and $R_{17B}$ is not particularly limited and examples thereof include 4 to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

$R_{15}$, $R_{16}$, $R_{17A}$, and $R_{17B}$ each preferably represent one of an alkyl group and an aryl group, and more preferably represent one of a methyl group, an ethyl group, a propyl group, a butyl group, and an unsubstituted and substituted phenyl group.

$X_2^-$ in the general formula (II) represents an anionic group. Here, the anionic group is not particularly limited and examples thereof include: halogen ions such as a fluoride ion, a chloride ion, a bromide ion, and an iodide ion; inorganic acid ions such as a sulfuric acid ion, a phosphoric acid ion, a nitric acid ion, a tetrafluoroboric acid ion, and a hexafluorophosphoric acid ion; Lewis acid-containing ions such as a tetrachloroaluminum ion; and organic acid ions such as an acetic acid ion, a lactic acid ion, a methanesulfonic acid ion, a benzenesulfonic acid ion, a p-toluenesulfonic acid ion, a trifluoroacetic acid ion, a trifluoromethanesulfonic acid ion, and a tetraphenylboric acid ion.

The anionic group represented by $X_2^-$ is preferably one of a chloride ion, a bromide ion, an iodide ion, a sulfuric acid ion, a nitric acid ion, and a methanesulfonic acid ion, and more preferably, in terms of ease of synthesis of the compound, one of a bromide ion and an iodide ion.

When $R_{11}$ represents one of a sulfonic acid group and a carboxylic acid group in a molecular structure represented by the general formula (II), there exists a tautomer represented by one of the following general formulae (II') and (II"). The structure represented by the general formula (II) of the staining compound of the present invention also encompasses a structure represented by, for example, one of the following general formulae (II') and (II").

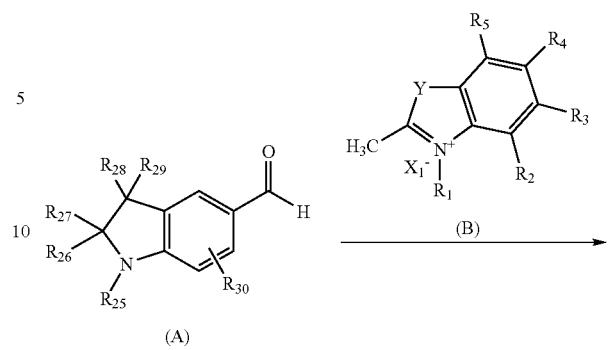

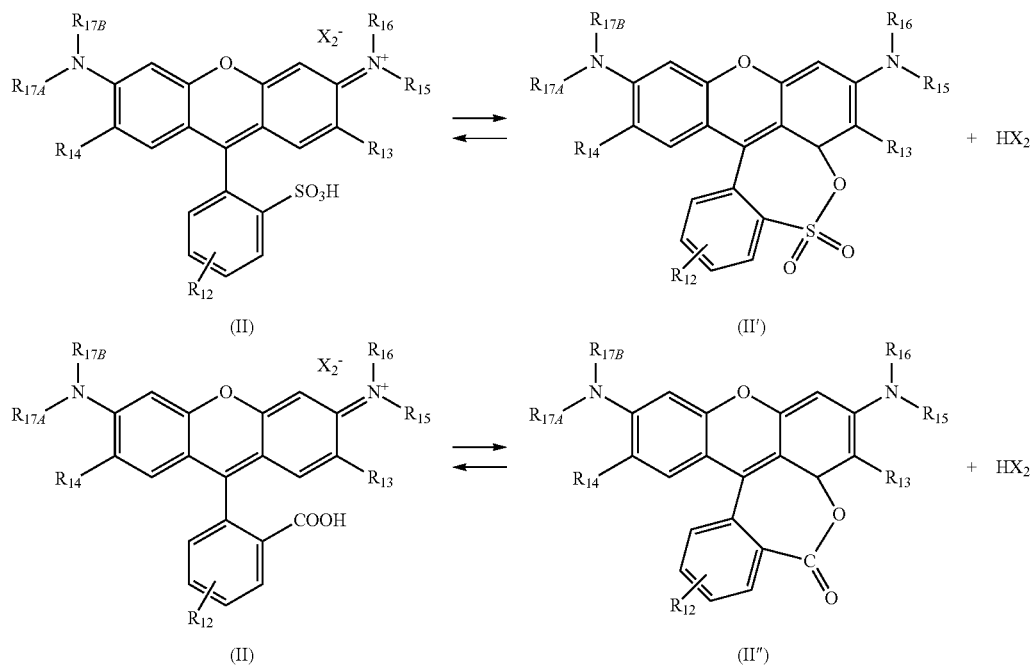

$R_{12}$ to $R_{16}$, $R_{17A}$, and $R_{17B}$ in the staining compound represented by one of the general formulae (II') and (II") have the same meanings as those of $R_{12}$ to $R_{16}$, $R_{17A}$, and $R_{17B}$ in the general formula (II).

The staining compound according to the present invention can be utilized for labelling of a hair cell as a staining agent that is retained by itself in the hair cell and stains the hair cell based on a structure of the compound itself that has a coloring property. Further, the staining compound according to the present invention can be used as a probe in such a form that a compound capable of producing an optical signal is further added to the compound, by utilizing a feature of the compound of being retained in a hair cell. The compound to be added may bonded directly or via a linker molecule. For the compound to be added, such a low molecular weight compound that can penetrate a cell membrane and permeate into a hair cell can be suitably used.

Next, a production method for the staining compound having a structure represented by the general formula (I) of the present invention is described below. The staining compound represented by the general formula (I) according to the present invention may be synthesized by a known method. An exemplary synthesis scheme is described below.

-continued

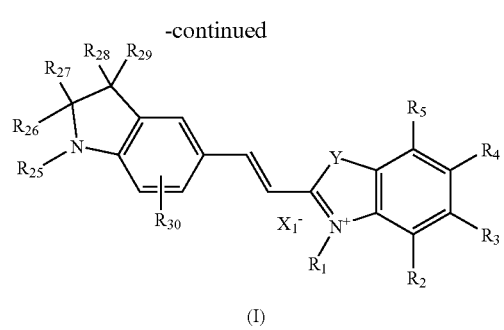

$R_1$ to $R_5$, $R_{25}$ to $R_{30}$, and $X_1^-$ in the above general formulae (I), (A), and (B) have the same meanings as those of $R_1$ to $R_5$, $R_{25}$ to $R_{30}$, and $X_1^-$ in the general formulae (I) to (IV).

The staining step can be easily performed by a known method (for example, Yakugaku Zasshi, 69, pp. 237-239, 1949, Indian Journal of Chemistry, Vol. 6, pp. 136-139, 1968, and Synthesis, pp. 37-38, 1976). A specific coupling method is not particularly limited, and a method described below is exemplified as one aspect.

That is, the coupling of an aldehyde derivative (A) and a compound (B) yields a staining compound (I).

The amount of the compound (B) to be used is 0.1 to 10-fold mol, preferably 0.5 to 3-fold mol, and more preferably 0.8 to 2-fold mol with respect to 1 mol of the aldehyde derivative (A).

This step may also be performed without using any solvent but is preferably performed in the presence of a solvent. The solvent is not particularly limited as long as it is not involved in the reaction, and examples thereof include: an ester-based solvent such as methyl acetate, ethyl acetate, isopropyl acetate, and butyl acetate; a nitrile-based solvent such as acetonitrile, propionitrile, and benzonitrile; an aromatic solvent such as benzene, toluene, xylene, ethylbenzene, chlorobenzene, and mesitylene; an ether-based solvent such as diisopropyl ether, methyl tert-butyl ether, and tetrahydrofuran; an alcohol-based solvent such as methanol, ethanol, n-propyl alcohol, iso-propyl alcohol, butyl alcohol, and diethylene glycol; a ketone-based solvent such as acetone and methyl ethyl ketone; dimethylformamide (DMF); dimethylsulfoxide (DMSO); water; and acetic acid. Preferred examples include an alcohol-based solvent such as methanol, ethanol, n-propyl alcohol, iso-propyl alcohol, butyl alcohol, and diethylene glycol, water, and acetic acid, and more preferred examples include ethanol, iso-propyl alcohol, diethylene glycol, and acetic acid. Further, two or more kinds of solvents may be used in mixture, and the mixing ratio may be arbitrarily set during use in mixture.

The amount of a reaction solvent to be used in this step is in the range of 0.1 to 1.000-fold weight, preferably 0.5 to 500-fold weight, and more preferably 1.0 to 150-fold weight with respect to the aldehyde derivative (A).

The reaction temperature at which this step is performed is in the range of −80° C. to 250° C., preferably −20° C. to 200° C., and more preferably −5° C. to 150° C. In general, the reaction is completed within 24 hours.

In this step, the reaction rapidly proceeds by the addition of an acid or a base as necessary. The acid to be used is not limited as long as it is not directly involved in the reaction, and examples thereof include: an inorganic acid such as hydrochloric acid, sulfuric acid, and phosphoric acid; an organic acid such as p-toluenesulfonic acid, formic acid, acetic acid, propionic acid, and trifluoroacetic acid; a strongly acidic ion-exchange resin such as AMBERLITE (Rohm and Haas Company) and AMBERLYST (Rohm and Haas Company); and an inorganic acid salt such as ammonium formate and ammonium acetate. More preferred is an inorganic acid salt such as ammonium formate and ammonium acetate, and still more preferred is ammonium acetate. The amount of the acid to be used is 0.001 to 50-fold mol, preferably 0.01 to 10-fold mol, and more preferably 0.1 to 5-fold mol with respect to 1 mol of the aldehyde derivative (A).

Specific examples of the base to be used in this step include: a metal alkoxide such as potassium tert-butoxide, sodium tert-butoxide, sodium methoxide, and sodium ethoxide; an organic base such as piperidine, pyridine, 2-methylpyridine, dimethylaminopyridine, diethylamine, diethylamine, isopropylethylamine, sodium acetate, potassium acetate, 1,8-diazabicyclo[5.4.0]undeca-7-ene (hereinafter, abbreviated as DBU), and ammonium acetate; an organic base such as n-butyl lithium and tert-magnesium chloride; and an inorganic base such as sodium borohydride, metallic sodium, sodium hydride, and sodium carbonate. Preferred examples include potassium tert-butoxide, sodium methoxide, sodium ethoxide, piperidine, dimethylaminopyridine, sodium acetate, and ammonium acetate, and more preferred examples include sodium methoxide, piperidine, sodium acetate, and ammonium acetate. The amount of the above-mentioned base to be used is 0.1 to 20-fold mol, preferably 0.5 to 8-fold mol, and more preferably 1.0 to 4-fold mol with respect to 1 mol of the aldehyde derivative (A).

After the completion of the reaction, the dilution with water, the acid deposition with hydrochloric acid, or the like may be performed to obtain a staining compound (I).

The obtained staining compound (I) may be subjected to a conventional method for isolation and purification of an organic compound. For example, after acid deposition has been performed by acidifying a reaction solution with hydrochloric acid and the like, a solid is separated by filtration, followed by neutralization with sodium hydroxide and the like and concentration. Thus, a crude product is obtained. In addition, the crude product is recrystallized from acetone, methanol, and the like, and purified by, for example, silica gel column chromatography. The purification may be performed by using one of those methods alone or by using two or more kinds thereof in combination to afford a product with high purity.

Next, a production method for a staining compound having a structure represented by the general formula (II) of the present invention is described below.

The staining compound represented by the general formula (II) according to the present invention can be synthesized according to a known method. An exemplary synthesis scheme is described below.

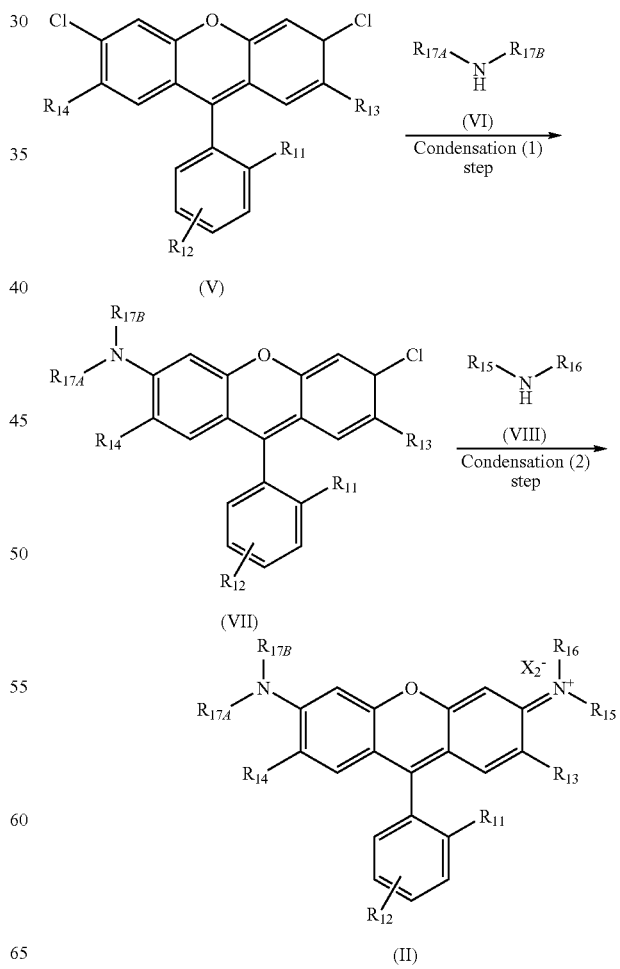

$R_{11}$ to $R_{16}$, $R_{17A}$, and $R_{17B}$ in the above general formulae (II) and (V) to (VIII) have the same meanings as those of $R_{11}$ to $R_{16}$, $R_{17A}$, and $R_{17B}$ in the general formula (II).

The staining step can be easily performed by a known method (for example, Japanese Patent Application Laid-Open No. 2008-94897). That is, the staining compound (II) of the present invention can be synthesized by a condensation (1) step and a condensation (2) step.

First, in the condensation (1) step, a compound (V) and a compound (VI) are subjected to heat condensation in an organic solvent (or in the absence of a solvent) in the presence of a condensation agent (or in the absence of a condensation agent) to afford a compound (VII). Next, the compound (VII) is subjected to second heat condensation with such a compound (VIII) as described above. Thus, a staining compound (II) according to the present invention is obtained.

A preferred organic solvent that can be used in the condensation (1) step of the condensation reaction of such a synthesis scheme as exemplified above is not particularly limited as long as the solvent is not involved in the reaction, and for example, methanol, ethanol, n-propanol, isopropanol, and n-butanol may be used alone or in mixture. A preferred organic solvent that can be used in the condensation (2) step is not particularly limited as long as the solvent is not involved in the reaction, and examples thereof include ethylene glycol, N-methylpyrrolidone, N,N-dimethylacetamide, N,N-dimethylformamide, dimethylsulfoxide, sulfolane, chlorobenzene, dichlorobenzene, trichlorobenzene, and nitrobenzene.

The reaction temperature at which the condensation (1) step is performed is in the range of 0° C. to 200° C., preferably 10° C. to 150° C., and more preferably 20° C. to 100° C. Further, the reaction temperature at which the condensation (2) step is performed is in the range of 50° C. to 250° C., preferably 100° C. to 230° C., and more preferably 150° C. to 220° C.

In the case of a compound where $R_{14}$ and $R_{15}$ in the general formula (II) are the same substituent to each other, and where $R_{16}$ and $R_{17}$ are the same substituent to each other, because the compounds (VI) and (VIII) in the scheme are identical to each other, the staining compound of the general formula (II) can be obtained in one condensation step from the compound (V). In this case, the reaction temperature conforms to that in the condensation (2) step.

The condensation agent to be used in the condensation step(s) is not particularly limited as long as the agent is not involved in the reaction, and may be selected from magnesium oxide, zinc chloride, and aluminum chloride, for example. The obtained staining compound (II) may be subjected to a conventional method for isolation and purification of an organic compound. For example, after acid deposition has been performed by acidifying a reaction solution with hydrochloric acid and the like, a solid is separated by filtration, followed by neutralization with sodium hydroxide and the like and concentration. Thus, a crude product is obtained. In addition, the crude product is purified by, for example, recrystallization from acetone, methanol, and the like, and silica gel column chromatography. The purification may be performed by using one kind of those methods alone or by using two or more kinds thereof in combination to afford a product with high purity.

Hereinafter, specific examples (1) to (70) of the present invention are described. However, the present invention is not limited to the following examples.

(1)

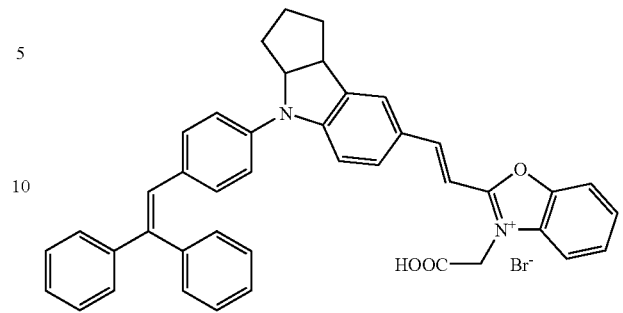

(2)

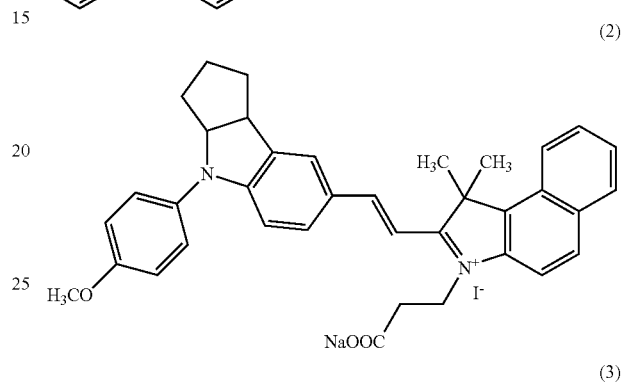

(3)

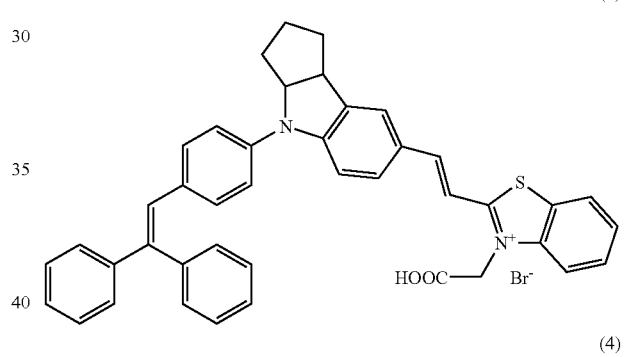

(4)

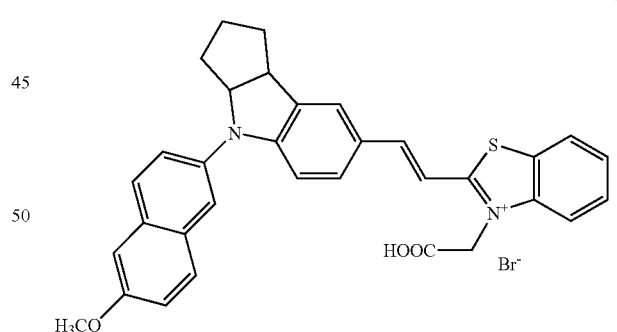

(5)

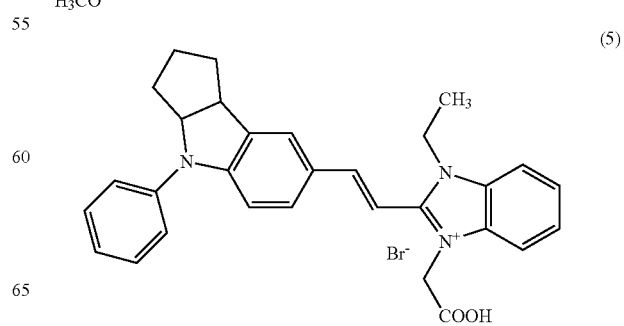

-continued
(6)
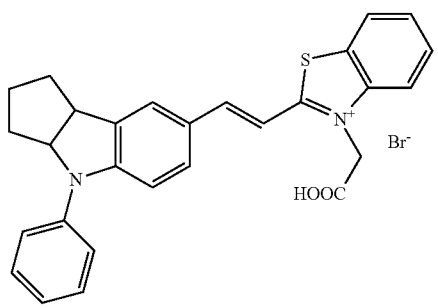
(7)
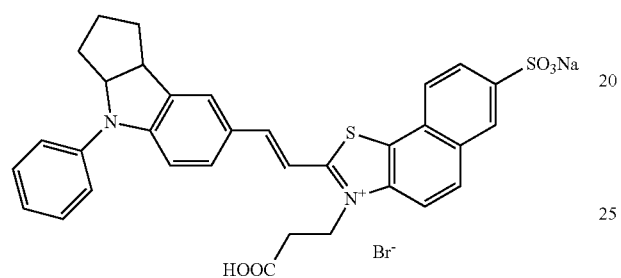
(8)
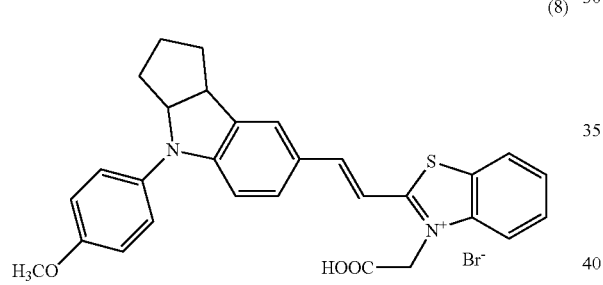
(9)
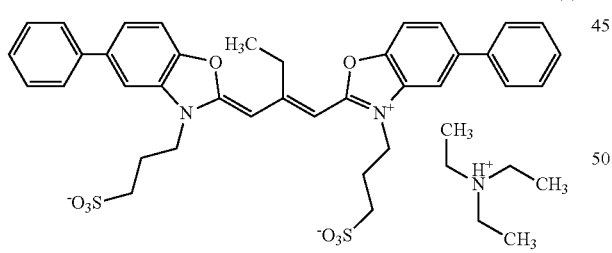
(10)
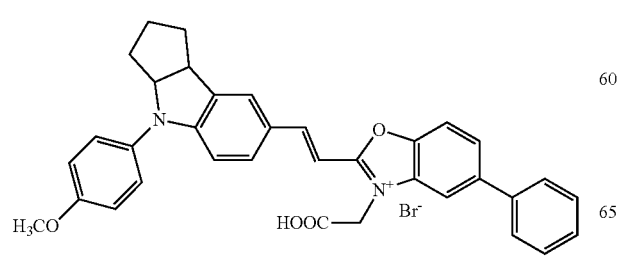
-continued
(11)
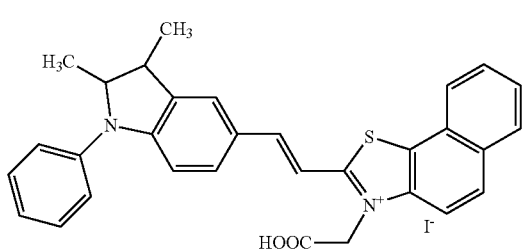
(12)
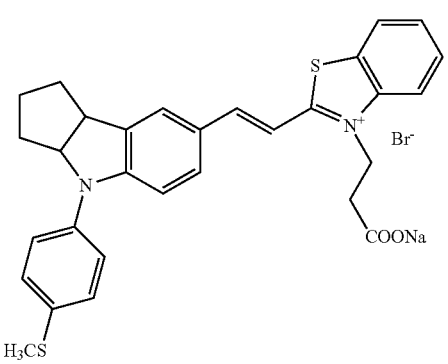
(13)
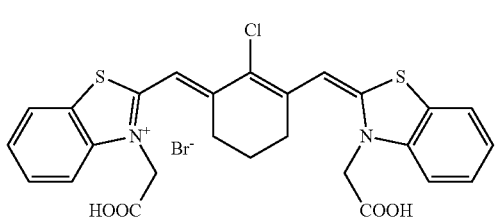
(14)
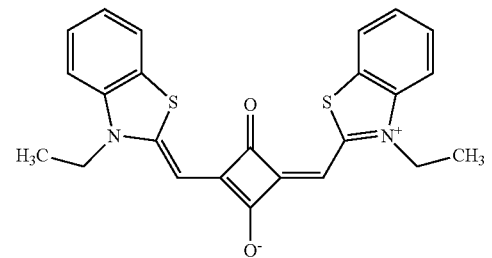
(15)
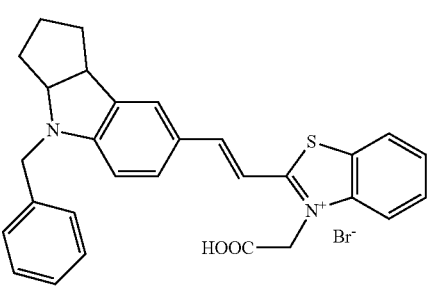

-continued
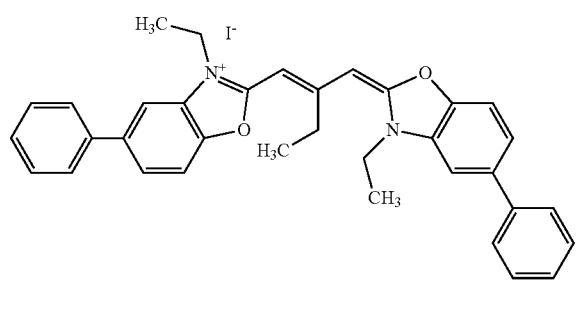
(16)
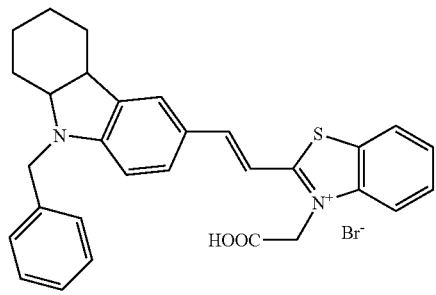
(17)
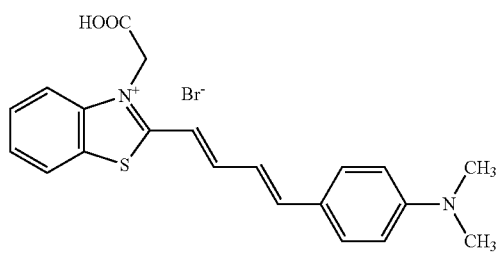
(18)
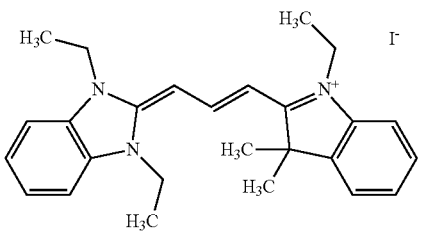
(19)
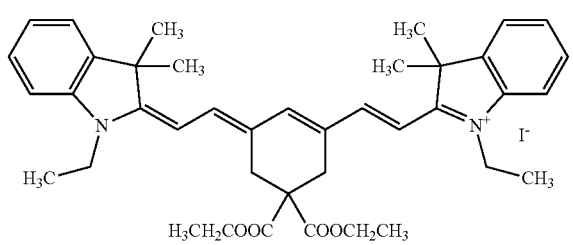
(20)
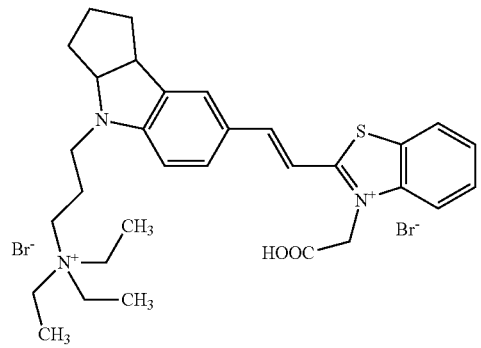
(21)
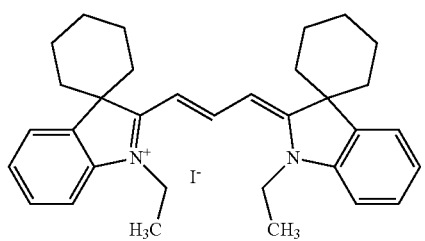
(22)
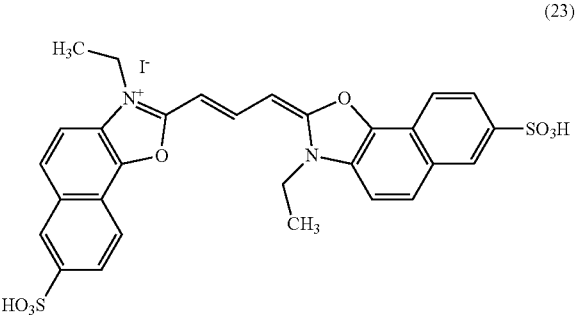
(23)
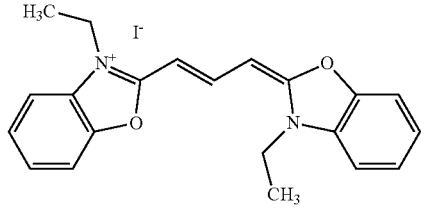
(24)
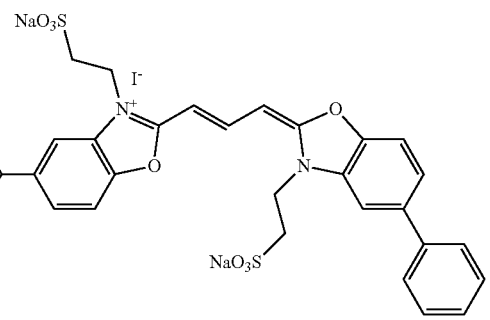
(25)

(26)
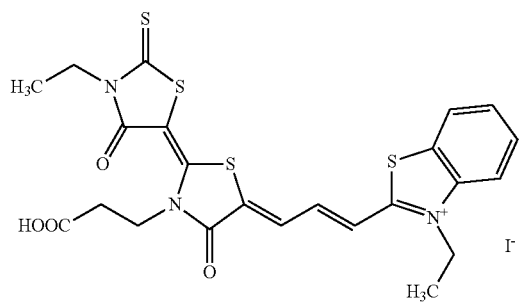
(27)
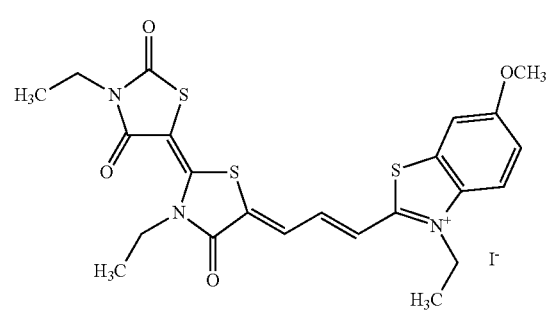
(28)
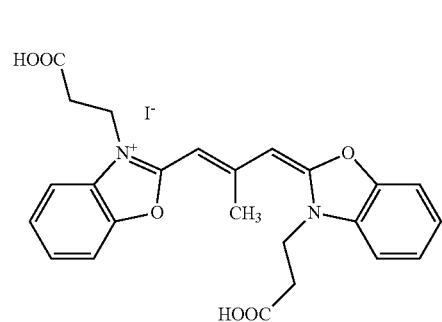
(29)
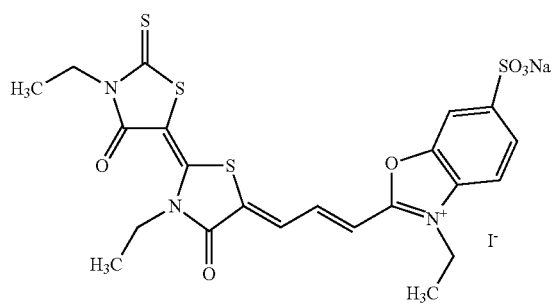
(30)
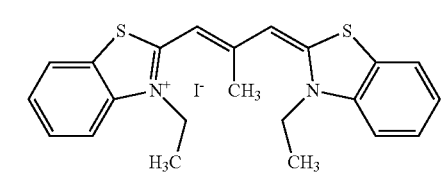
(31)
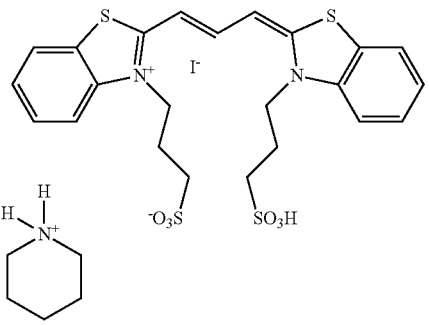
(32)
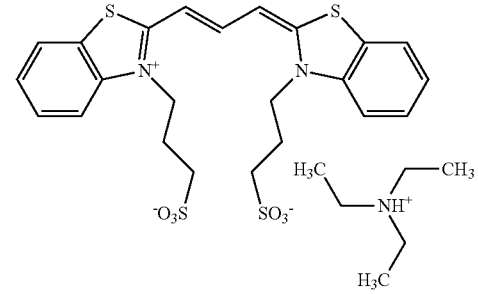
(33)
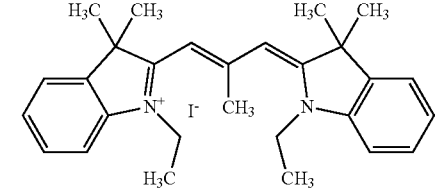
(34)
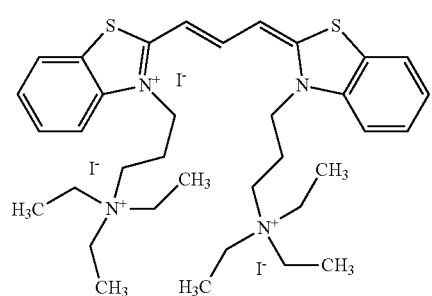
(35)
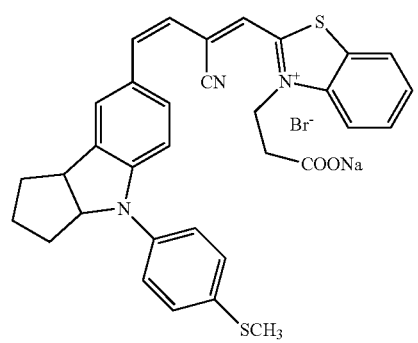

(36)
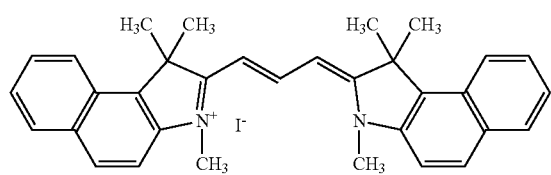
(37)
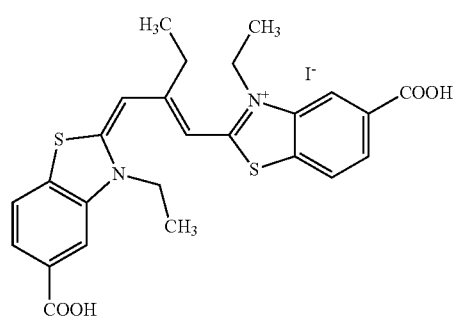
(38)
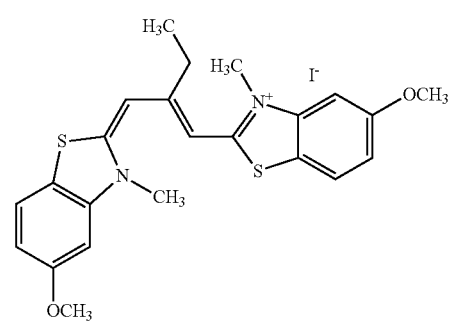
(39)
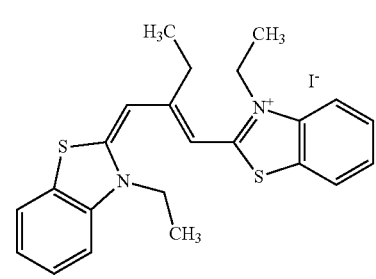
(40)
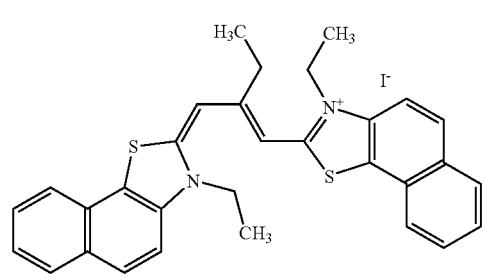
(41)
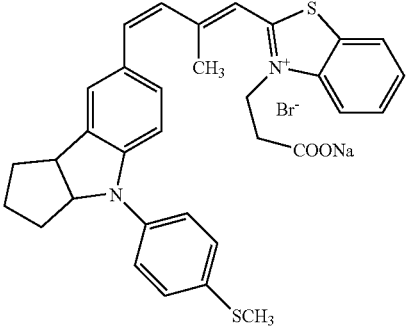
(42)
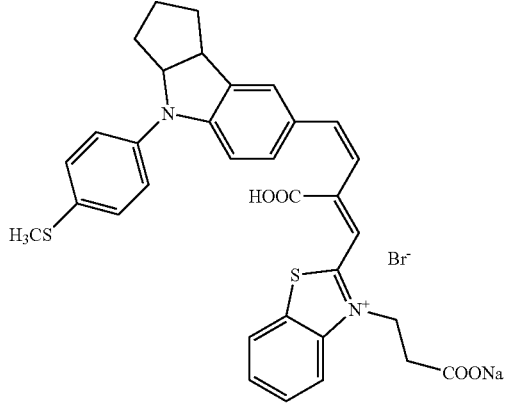
(43)
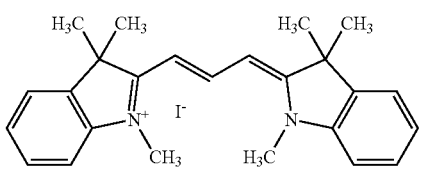
(44)
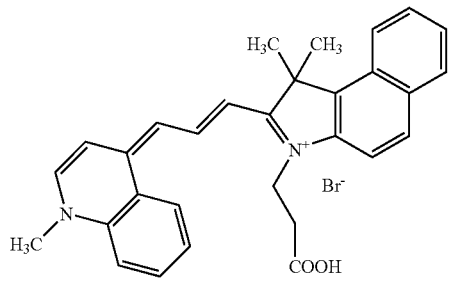
(45)
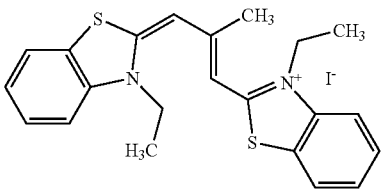

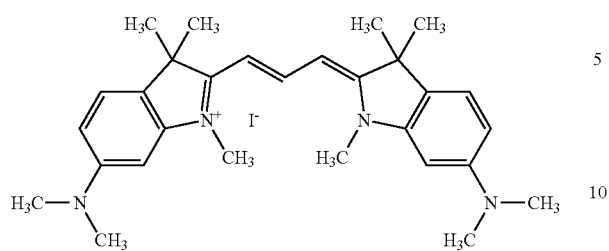
(46)
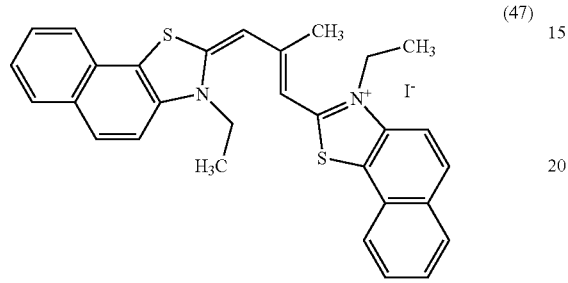
(47)
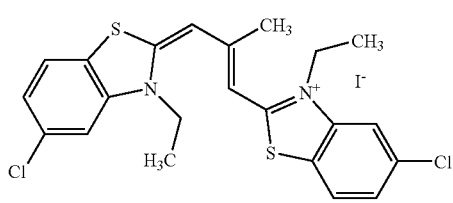
(48)
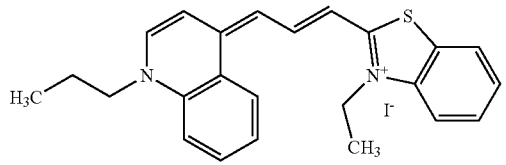
(49)
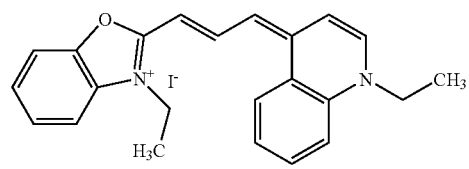
(50)
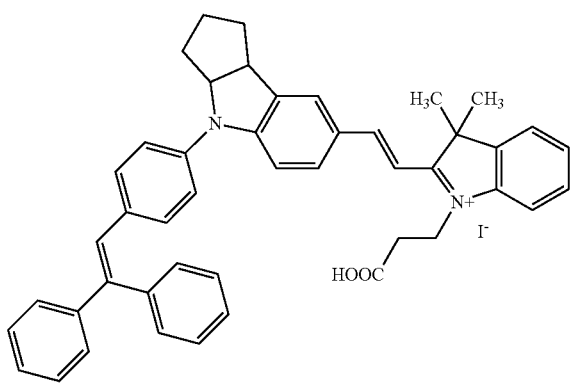
(51)
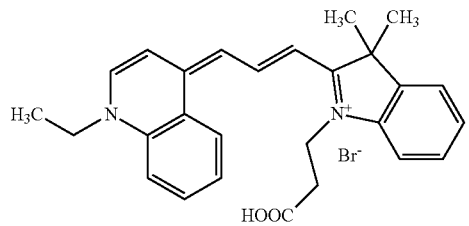
(52)
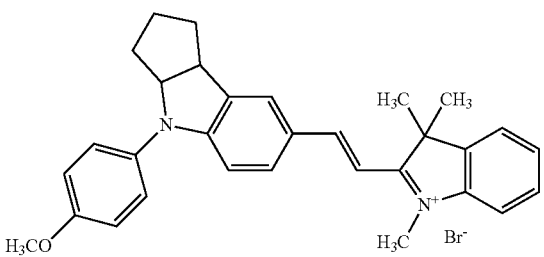
(53)
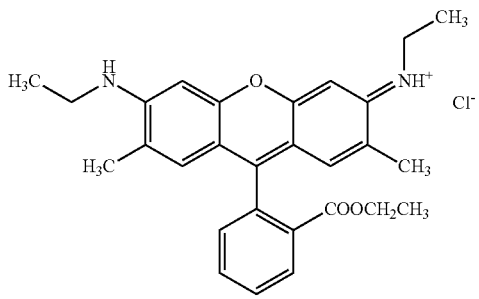
(54)
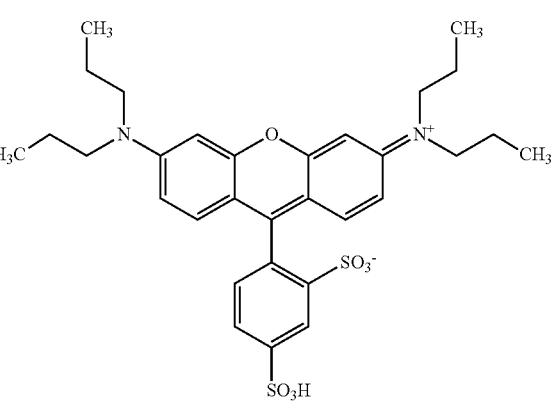
(55)
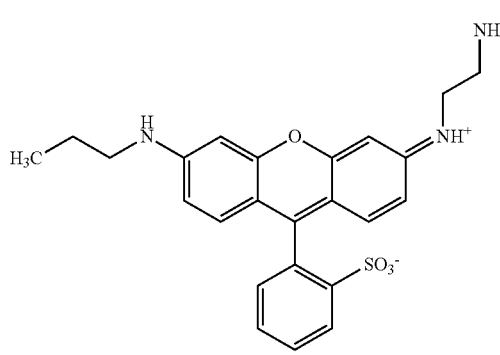
(56)

-continued
(57)
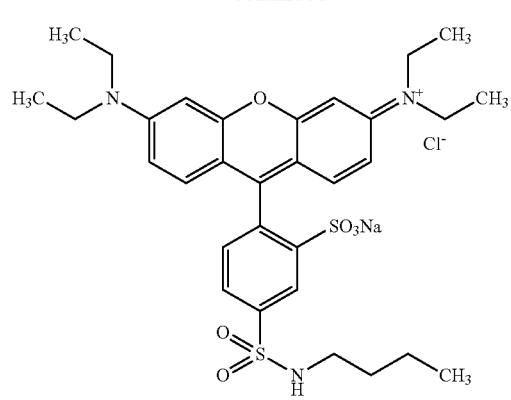
(58)
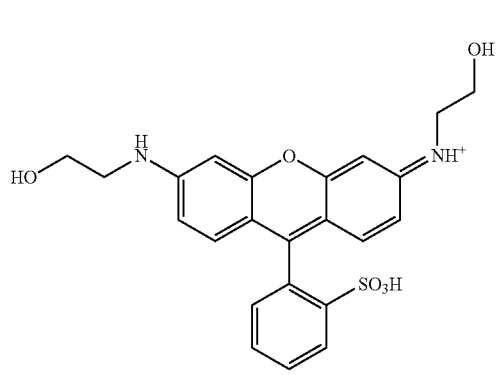
(59)
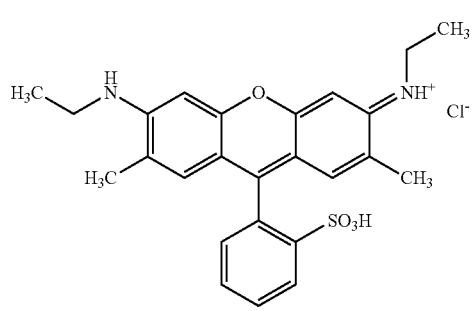
(60)
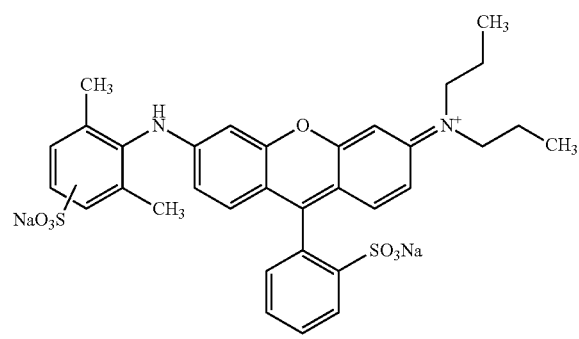
-continued
(61)
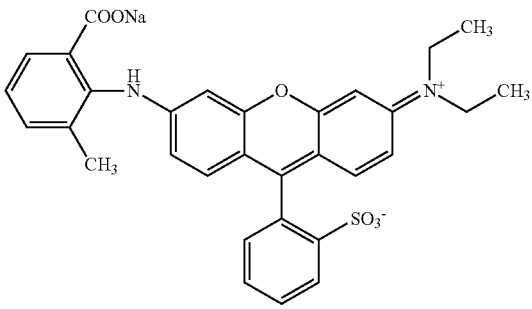
(62)
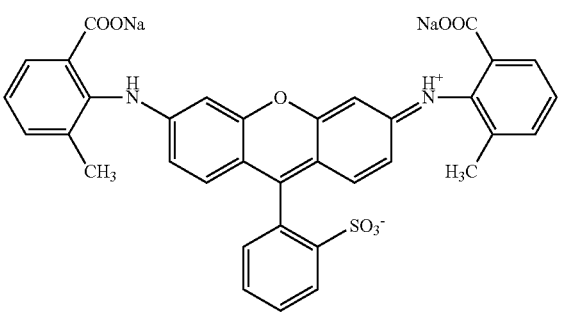
(63)
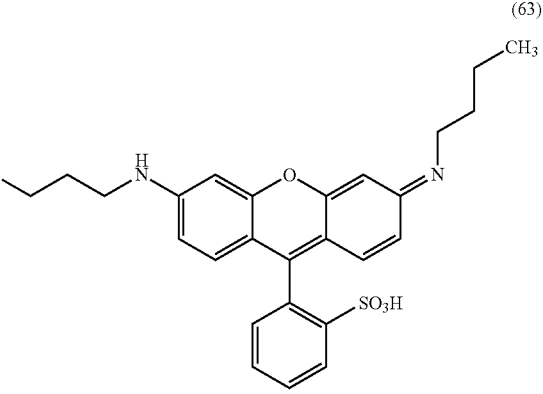
(64)
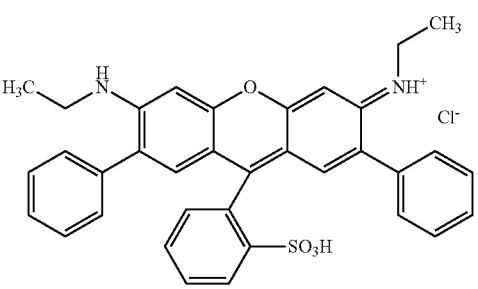
(65)
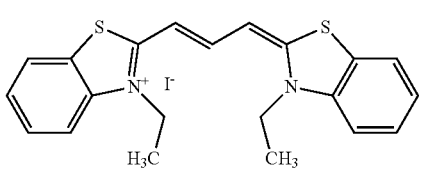

-continued

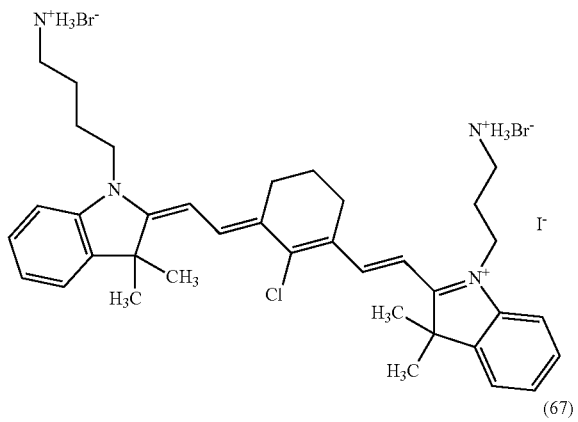
(66)

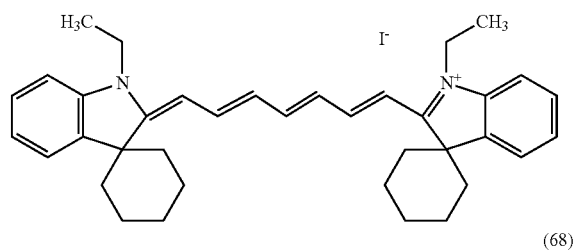
(67)

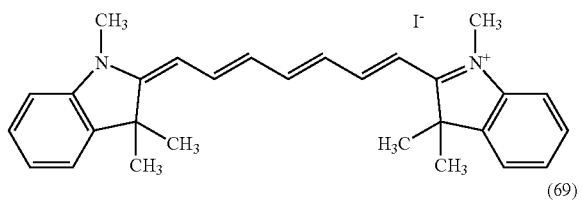
(68)

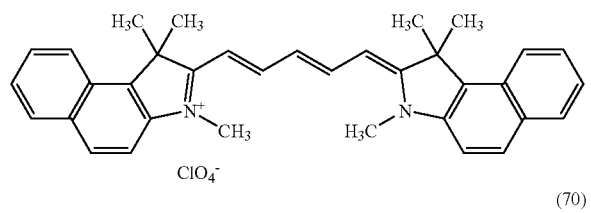
(69)

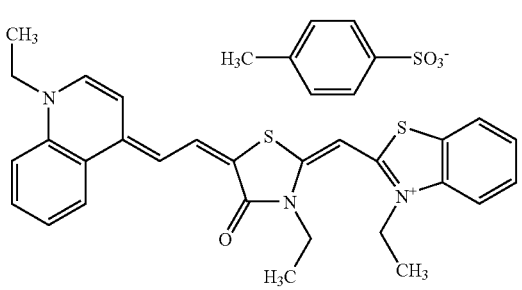
(70)

A hair cell staining (labelling) solution of the present invention is prepared by dissolving the probe for a hair cell of the present invention in an appropriate solvent. The solvent is not particularly limited as long as it has no influence on a living body, but an aqueous liquid with high biocompatibility is preferred. Examples of the solvent include: water; physiological saline; a buffer such as a phosphoric buffer saline (PBS) and Tris; an alcohol-based solvent such as ethanol, ethylene glycol, and glycerin; an organic solvent such as N,N-dimethylsulfoxide (hereinafter, abbreviated as DMSO); a cell culture medium such as D-MEM and HBSS; and an infusion solution such as a lactated Ringer's solution, and particularly preferred is a solvent containing 50% or more of water. Further, two or more kinds of those solvents may be used in mixture.

To the hair cell staining (labelling) solution, preferably added is at least one of a humectant, a surface tension adjusting agent, and a thickener, for example. If a salt concentration and a pH suitable for a living body must be controlled, one of salts such as sodium chloride, various pH adjusting agents, preservatives, antibacterial agents, sweeteners, and flavors may be appropriately added, for example.

The pH adjusting agent is not particularly limited, but preferably adjusts a pH to 5 to 9. Examples thereof include hydrochloric acid, acetic acid, phosphoric acid, citric acid, malic acid, sodium hydroxide, and sodium bicarbonate.

An organism to be stained with the probe for a hair cell of the present invention is not particularly limited as long as the organism has a hair cell, and examples thereof include: small bony fishes such as Japanese putter fish, Japanese rice fish, and Zebrafish; a small animal such as a rat and a mouse; a large animal such as a primate, a pig, and a dog; and a human. In addition to an individual organism, there are exemplified a tissue and a tissue section derived from the organism, and a culture cell derived from the organism.

The form of the probe for a hair cell of the present invention is not particularly limited, and the probe for a hair cell can be used in a form such as a liquid, a granule, a tablet, a capsule, and a patch.

The administration route of the probe for a hair cell for staining a hair cell present in the auditory organs is not particularly limited, and the probe for a hair cell can be orally or parenterally administered. Systemic administration is also possible, but local administration is preferred in order to enhance an effect of staining properties.

In the case of local administration, the probe for a hair cell can be directly administered to a tissue with a hair cell (i.e. inner ear), or may be administered through the external auditory canal and the middle ear. Further, the probe for a hair cell may be administered via the endolymphatic sac, the endolymphatic duct, and the auditory capsule. Local administration is more preferably performed by exposure of the probe for a hair cell to a living body (a liquid etc.), and administration to the living body including intravascular administration such as intravenous administration and intraarterial administration, oral administration, sublingual administration, intrarectal administration, intraperitoneal administration, transdermal administration, subcutaneous administration, intradermal administration, intravesical administration, endotracheal (intrabronchial) administration, intraocular administration, transnasal administration, and intraaural administration, which utilize means such as injection, catheter infusion, nebulization, application, and the like. In addition, such an apparatus as described in, for example, U.S. Pat. Nos. 5,476,446 and 5,350,580 may be used.

The dosage of the probe for a hair cell is not particularly limited as long as a target site can be finally detected, and can be appropriately increased or decreased depending on the kind of the target site and the probe to be used. In particular, when the probe for a hair cell is administered to an individual organism, the smallest possible amount is preferred. Further, when being exposed to a tissue and a cell, the probe for a hair cell may be used in an amount that has selectivity for tissue staining (labelling) and is easy to be distinguished.

The concentration of the probe for a hair cell to be used is in the range of generally 0.001 nM to 1,000 µM and preferably 0.01 nM to 100 µM.

The administration form, administration route, and dosage for an animal are appropriately selected depending on the body weight and condition of an animal of interest.

An evaluation method for an auditory function of the present invention involves staining a hair cell of an organism with the probe for a hair cell of the present invention, and then observing, detecting, or measuring a staining condition of the hair cell. The observation, measurement, and detection in the evaluation method for an auditory function of the present invention are performed by a method known to those skilled in the art.

An observation method for a staining condition to be used in the present invention is not particularly limited as long as the method has no influence on both the organism and the probe for a hair cell, and is a method of capturing a condition and a change of the organism as an image. Examples of the observation method include infra red imaging, which involves irradiating an organism with one of visible light, near-infrared light, and infrared light, and observing with a camera, CCD, and the like, laser microscopy; fluorescent imaging, fluorescent microscopy, fluorescent endomicroscopy, confocal endomicroscopy, multiphoton-excited fluorescence microscopy, narrow band imaging, and optical coherence tomography (OCT), each of which involves observing fluorescence derived from an organism with a fluorescence endoscope etc. by irradiating a biological specimen with excitation light from an excitation light source; and further, soft X-ray microscopy.

The probe for a hair cell of the present invention may be labelled with a radionuclide.

The probe for a hair cell labelled with a radionuclide may be imaged with one of autoradiography, positron emission tomography (PET), and single photon emission computed tomography (SPECT). Further, the probe for a hair cell may be detected by magnetic resonance imaging (MRI) utilizing an MR signal derived from a fluorine nucleus and $^{13}C$. In addition, the probe for a hair cell can be imaged by using a compton camera (GREI) capable of simultaneously imaging multiple molecules as a next-generation molecular imaging apparatus. A distribution condition of a hair cell can be time-dependently measured and imaged in a noninvasive manner by those methods. Further, a probe for a biological specimen can be quantitatively determined by using, for example, a liquid scintillation counter, an X-ray film, and an imaging plate.

Further, the measurement of the blood (or urinary or fecal) concentration of the probe for a hair cell labelled with a radioisotope such as $^{14}C$ by using, for example, accelerator mass spectrometry (AMS) can provide pharmacokinetic information (such as area under the blood concentration-time curve (AUC), blood concentration half life ($T_{1/2}$), maximum blood concentration ($C_{max}$), time-to-maximum blood concentration ($T_{max}$), distribution volume, first-pass effect, bioavailability, and urinary and fecal excretion rate) on an unchanged product and a metabolite of a labelled substance.

The radionuclide is not particularly limited and may be appropriately selected depending on the usage mode.

Specifically, in the case of measurement with PET, a positron emitting nuclide such as $^{11}C$, $^{14}C$, $^{13}N$, $^{15}O$, $^{18}F$, $^{19}F$, $^{62}Cu$, $^{68}Ga$, and $^{78}Br$ may be used, for example. Preferred examples include $^{11}C$, $^{13}N$, $^{15}O$, and $^{18}F$, and particularly preferred examples include $^{11}C$ and $^{18}F$. Further, in the case of measurement with SPECT, a γ-ray emitting nuclide such as $^{99m}Tc$, $^{111}In$, $^{67}Ga$, $^{201}Tl$, $^{123}I$, and $^{133}Xe$ may be used, for example. Preferred examples include $^{99m}Tc$ and $^{123}I$. In addition, in the case of measurement of animals other than a human, a radionuclide having a longer half life such as $^{125}I$ may be used, for example. In the case of measurement with GREI, one of $^{131}I$, $^{85}Sr$, and $^{65}Zn$ may be used, for example.

The radionuclide may be contained in or bonded to the compound represented by one of the general formula (I) and (II). A labelling method with the radionuclide is not particularly limited, and at least one part of elements of which the compound represented by one of the general formula (I) and (II) is formed may be replaced by or bonded to the radionuclide.

When the compound represented by one of the general formula (I) and (II) is labelled with the radionuclide, the compound preferably has radioactivity of about 1 to 100 μCi per mM.

In this case, the dosage of the probe for a hair cell to be used is not particularly limited as long as it has no influence, and is appropriately selected depending on the kind of the compound and the kind of the radionuclide used as a label.

For example, for an adult human, the amount of the probe for a hair cell to be used is 0.0001 μg to 1,000 μg and preferably 0.01 μg to 10 μg per day.

The wavelength of excitation light to be used in the present invention is not particularly limited as long as it has no influence on both the organism and the probe for a hair cell, varies depending on the kind of the probe to be used, and is not particularly limited as long as the probe of the present invention efficiently fluoresces. The wavelength is generally 200 to 1,010 nm, preferably 400 to 900 nm, and more preferably 480 to 800 nm. The wavelength in the case of using light in a near-infrared area is generally 600 to 1,000 nm and preferably 680 to 800 nm in which wavelength biological permeability is excellent.

A fluorescence excitation light source to be used in the present invention is not particularly limited as long as the light source has no influence on both the organism and the probe for a hair cell, and various laser light sources may be used. Examples thereof include a dye laser, a semiconductor laser, an ion laser, a near-infrared pulse laser, a fiber laser, a halogen lamp, a xenon lamp, and a tungsten lamp. Further, the use of various optical filters allows the acquisition of preferred excitation wavelengths and the detection of only fluorescence.

As mentioned above, if an image of an individual organism is captured in such a condition that the organism has been irradiated with excitation light to cause light emission inside the individual organism, a light emitting site can be easily detected. Further, a bright field image obtained by irradiation with visible light and a fluorescence image obtained by irradiation with excitation light can be combined by using an image processing unit to observe the individual organism in more detail.

Many of the probes for a hair cell of the present invention each have large Stokes' shift, and hence can identify a hair cell clearly. The term "Stokes' shift" as used herein represents a difference between the maximum excitation wavelength and the maximum fluorescence emission wavelength. In general, a small Stokes' shift tends to generate a measurement error due to excitation light and its scattering light.

Next, an evaluation method for the auditory toxicity of a chemical substance by using the probe for a hair cell of the present invention is described in detail below. That is, the evaluation method involves the following steps: administering a chemical substance to an organism; bringing the organism into contact with a probe for a hair cell; and observing fluorescence derived from the probe for a hair cell by irradiating the organism with excitation light. Thus, the auditory toxicity of a chemical substance can be evaluated (screening method).

First, a step of administering a chemical substance to an organism is described.

The organism to be used in this step is not particularly limited, and the use of small bony fishes such as Zebrafish allows the high-throughput evaluation for the auditory toxicity of each of various chemical substances, for example.

In recent years, in U.S. and U.K., Zebrafish has been already recognized as a third model animal following a mouse and a rat. Zebrafish is easily optically observed because Zebrafish has a feature that a process in which the respective parts (organs such as heart, liver, kidney, and gastrointestinal tract) are differentiated and formed from a fertilized embryo can be observed through its transparent body. Further, it is being clarified that, in a comparison to human, Zebrafish has an 80% homology in terms of the full genome sequence, is almost the same in terms of the number of genes, and is very similar also in terms of the development and structure of principal organs and tissues. Therefore, the auditory toxicity of a chemical substance screened by using Zebrafish as a model animal is highly likely to be applicable to a human. In addition, a sensory hair cell lies deep within a temporal bone portion in a vertebrate such as a mouse. Thus, the sensory hair cell is anatomically difficult to handle, and is hardly observed and subjected to an additional manipulation in an experiment. In contrast, Zebrafish has a sensory hair cell of the inner ear, which can be clearly observed even in a developmental stage of embryo after spawning. Zebrafish also has a sensory hair cell in organs present on the skin surface called lateral line organs. Thus, it is possible to easily observe and manipulate the hair cell. Each of the lateral line organs serves as a sensor of the movement of water, and also shares a common origin with the inner ear. Therefore, Zebrafish is suitable for screening as a model animal.

A chemical substance to be evaluated by an evaluation method for the auditory toxicity of a chemical substance of the present invention means a collective name of substances, each of which may have a biological action. The chemical substance is not particularly limited and examples thereof include a pharmaceutical, an organic compound, a therapeutic agent, an investigational drug, an agricultural chemical, a cosmetic, an environmental pollutant, and an endocrine disruptor.

A method of administering the chemical substance to Zebrafish is not particularly limited. When the chemical substance is water-soluble, there is given a method of allowing the chemical substance to coexist in feeding water, and when the chemical substance is non-water-soluble, there is given one of a method of allowing the chemical substance alone to disperse and coexist in feeding water, a method of allowing the chemical substance and a trace amount of a surfactant or DMSO to coexist, and a method of orally administering the chemical substance mixed in a feed for Zebrafish, and a method of parenterally administrating the chemical substance with injection and the like. Preferably, there is given a method of allowing the chemical substance to coexist in feeding water, which can be easily performed.

Next, there is described a step of bringing an organism into contact with a probe for a hair cell.

After the administration of a chemical substance to Zebrafish, if necessary, the chemical substance exposed is removed, and then at least one kind of the probe for a hair cell of the present invention is utilized for staining a hair cell of Zebrafish. In this step, a method of administering the probe for a hair cell to Zebrafish is not particularly limited. When the probe for a hair cell is water-soluble, there is given a method of allowing the probe for a hair cell to coexist in feeding water, and when the probe for a hair cell is non-water-soluble, there is given one of a method of allowing the probe for a hair cell alone to disperse and coexist in feeding water, a method of allowing the probe for a hair cell and a trace amount of a surfactant or DMSO to coexist, a method of orally administering the probe for a hair cell mixed in a feed for Zebrafish, and a method of parenterally administering the probe for a hair cell with injection and the like. Preferably, there is given a method of allowing the probe for a hair cell to coexist in feeding water, which can be easily performed.

The dosage of the probe for a hair cell is not particularly limited as long as a target site can be finally detected, and may be appropriately increased or decreased depending on the kind of the target site and the probe to be used. In particular, in the case of administration to an individual organism, the smallest possible amount is preferred. Further, in the case of exposure to a tissue and a cell, an amount that has selectivity for tissue staining and is easy to be distinguished may be used.

Next, there is described a step of observing fluorescence derived from the probe by irradiating the organism with excitation light.

The wavelength of excitation light to be used in this step is not particularly limited as long as it has no influence on both the organism and the probe for a hair cell, varies depending on the kind of the probe to be used, and is not particularly limited as long as the probe of the present invention efficiently fluoresces. The wavelength is generally 200 to 1,010 nm, preferably 400 to 900 nm, and more preferably 480 to 800 nm. The wavelength in the case of using light in a near-infrared area is generally 600 to 1,000 nm and preferably 680 to 800 nm in which biological permeability is excellent.

A fluorescence excitation light source to be used in this step is not particularly limited as long as the light source has no influence on both the organism and the probe for a hair cell, and various laser light sources may be used. Examples thereof include a dye laser, a semiconductor laser, an ion laser, a fiber laser, a halogen lamp, a xenon lamp, and a tungsten lamp. Further, the use of various optical filters allows the acquisition of preferred excitation wavelengths and the detection of only fluorescence.

As described above, the auditory function of Zebrafish is evaluated by observing, detecting, or measuring a staining condition in such a condition that light has emitted in a hair cell of Zebrafish by irradiating Zebrafish with excitation light. The auditory toxicity of the chemical substance subjected to a test can be screened based on the evaluation.

Many special mechanoreceptors called lateral line organs exist on the body surface of Zebrafish and form a lateral line system as a whole. An individual end organ belonging to the system serves as a neuromast and is innervated by a branch of a specific cranial nerve. Embryologically, the neuromast and a nerve distributed in the neuromast are derived from placodes resulting from the thickening of an ectoderm of an embryo. The placodes are formed of approximately 120 cells, and are differentiated from primordia moving from the head toward the tail in a period of 20 hours to 40 hours after fertilization. The primordia leave 7 to 9 proneuromasts and interneuromast cells connecting the proneuromasts with each other along the movement route. After that, second smaller primordia move along the same route and leave 2 or 3 proneuromasts on the movement route. A posterior lateral line neuromast gradually matures from the head toward the tail, and by Day 5 of development, a functional hair cell is included in 9 to 11 neuromasts. After that, the system becomes complicated through the additional development of the neuromast and the growth and elongation of existing clusters.

The use of the probe for a hair cell of the present invention allows the staining, staining with various patterns, and identification of not only a Zebrafish neuromast (big size), which has been conventionally reported, but also a microorgan (neuromast of small size) on the body surface, which has not been visualized thus far.

The staining of the neuromast with different colors can be utilized for the evaluation for the toxicity of a chemical substance with respect to a difference in the type of hair cell injuries in a developmental process, and the evaluation for the auditory toxicity of a chemical substance with respect to a hair cell precursor, for example. An evaluation method (screening method) for the auditory toxicity of a chemical substance of the present invention is highly excellent in terms of a speed and a cost compared with a method using a mouse, a rat, and the like because Zebrafish is easy in its feeding and propagation and low in its market price, and has principal organs and tissues, the basic structures of which are formed in 48 to 72 hours after fertilization.

Zebrafish is not limited to wild-type Zebrafish and various disease-based models of Zebrafish may be used depending on the purpose of screening. In the case of an auditory disease-based model, the model can be applied for screening for finding out an effect and toxicity of a new drug candidate compound by observing a hair cell by using the probe for a hair cell according to the present invention as an index. Examples of the auditory disease-based model include, but not particularly limited to, a model of Zebrafish such as a drug-induced hearing loss model and an inherited hearing loss model.

In a vertebrate such as a mouse, a sensory hair cell lies deep within a temporal bone portion. Thus, the sensory hair cell is anatomically difficult to handle, and is relatively hardly observed and subjected to an additional manipulation in an experiment. In order to visualize the sensory hair cell of a vertebrate including a human, out of the probe for a hair cell of the present invention, particularly preferred are an agent that fluoresces in a near-infrared area and an agent that has been labelled with a radionuclide. This is because, in case of using the agent that fluoresces in a near-infrared area, near-infrared light has no absorption with water and hemoglobin in the area, and easily transmits a body tissue, and as a result, test diagnosis can be performed in the range of a thickness of 10 to 20 cm. Further, the agent that has been labelled with a radionuclide can image a condition of a hair cell in a noninvasive manner by using PET, PET-CT, SPECT, and MRI, for example.

The probe for a hair cell of the present invention can be used as a diagnosis drug for an auditory function disease. Further, there can be provided a diagnostic composition for an auditory function containing, as an active agent, the probe for a hair cell of the present invention. The hair cell that has suffered an injury is difficult to retrieve. It is also said that, in a human, once the number of the hair cell is reduced, the number is extremely difficult to increase. Also from such a viewpoint, there is a need for finding out diseases through early diagnosis.

Examples of the auditory function disease include, but not particularly limited to, peripheral sensorineural auditory impairment (hearing reduction and hearing loss), tinnitus, vertigo, feeling of fullness in the ear, and equilibrium loss. Examples of hearing loss include, but not particularly limited to, age-related hearing loss, sensorineural hearing loss, conductive hearing loss, sudden hearing loss, noise-induced hearing loss, and acoustic trauma hearing loss, and acute hearing loss such as Meniere's disease, delayed endolymphatic hydrops, perilymph leak, drug-induced hearing loss, viral labyrinthitis, acoustic neuroma, and functional hearing loss. For high precision diagnosis and treatment method for those auditory function diseases, the application development such as a diagnosis with the staining properties of the hair cell is expected. Further, when the regeneration of the hair cell is attempted by using, for example, a gene treatment, and an ES cell and an iPS cell, the application development such as a following diagnosis of the hair cell is expected by utilizing the staining properties of the hair cell.

The probe for a hair cell of the present invention can be used for screening by the staining properties of a tissue and a cell taken out from a biological specimen (in vitro). In addition, the application development such as development of high precision diagnosis and treatment method is expected by utilizing staining properties of the probe for a hair cell. For example, it is expected that the probe for a hair cell can be used for cytology involving sampling one part of tissues and cells as targets in a trace amount by aspiration with a puncturing cytodiagnostic device and the like, staining the sample with the probe for a hair cell of the present invention, and assessing the form, kind, and benignancy and malignancy, and the like of the cell.

Further, for example, the introduction of an optical fiber into the tympanum through the tympanic membrane dissected from the external auditory canal or through the Eustachian tube from the epipharynx, the irradiation of one of a vestibular window portion, a cochlea portion, and a semicircular canal portion with excitation light via the optical fiber, and the acquisition of fluorescence allows in vivo acquisition of a hair cell labelling signal and a diagnosis for an auditory function disease based on the signal. The human inner ear is anatomically located in a pit of the skull, and hence, there is no need to worry about light shielding by the bone during light irradiation from the tympanum. Further, because the tympanum is generally filled with a gas, the absorption of near-infrared light by a liquid can be as minimum as absorption by lymph with which one of the vestibular window portion, the cochlea portion, and the semicircular canal portion is filled. Near-infrared light with generally used intensity has a permeability of 10 to 20 cm with respect to a living body, and hence, the probe for a hair cell having absorption or fluorescence in a near-infrared area can be suitably used as a component of a diagnostic drug for an auditory function of the present invention. Meanwhile, conventionally known probes for a hair cell such as DASPEI and FM1-43 have no absorption and fluorescence in a near-infrared area.

An image diagnosis of an auditory function using the probe for a hair cell of the present invention may complement conventional physiological function tests. As a physiological function test of hearing, there are exemplified: a threshold for air conduction and bone conduction of a pure sound, a speech reception threshold, and a speech discrimination ability; tympanometry; and a stapedial reflex test including impedance audiometry. Those tests are being used for assessment of hearing loss. The combination of an image using the diagnostic composition for an auditory function of the present invention allows the utilization of objective diagnosis information which may complement the physiological function tests which tend to be dependent on subjectivity of each of patients. Further, there is provided an auditory function diagnosis system formed of a combination of the probe for a hair cell of the present invention and a light signal detecting unit such as an optical fiber. The auditory function diagnosis system may further include units for imaging and analyzing the obtained light signal.

The probe for a hair cell of the present invention includes an agent that stains not only a somatic portion but also an axon portion of the hair cell. The demyelination of the axon portion of an auditory neuron is known as one of causes of hearing loss. The type of hearing loss can be assessed by evaluating both the staining properties of the somatic portion and the staining properties of the axon portion of the hair cell based on an imaging method for a hair cell of the present invention.

For the purpose of improving otorrhea and hearing loss due to chronic otitis media, a treatment called tympanoplasty may be performed. Further, for the purpose of extirpating a tumor and treating an infection, a treatment called labyrinthoplasty may be performed. Those operation techniques involve incising the skin at the postauricular root, trimming the bone to remove an inflammation in the bone, and restoring the tympanic membrane and the bone. As risks of those operation techniques, there are exemplified inner ear symptoms such as vertigo, tinnitus, and hearing loss. However, in the operation, if a retention degree of an auditory function is monitored by using the diagnostic composition for an auditory function of the present invention, an image diagnosis can be performed in an operation, leading to a more safe operation.

In particular, in the case of infants and senior adults with dementia who can hardly communicate with each other, animals, and the like, the diagnostic composition for an auditory function is expected to be used as a test reagent for an auditory function based on ex vivo staining properties using a hair cell extirpated and cultured as one means for auditory test.

The diagnostic composition for an auditory function of the present invention contains, as an active agent, at least one of the probe for a hair cell of the present invention. The composition is not particularly limited. The use of a substance for diagnosis labelled with the probe for a hair cell of the present invention is possible, and the use and application as a medicament for diagnosis containing the substance for diagnosis are also possible. Further, the use of the medicament for diagnosis containing the probe for a hair cell labelled with a radionuclide allows the hair cell to be easily imaged with one of PET, SPECT, and MRI, for example.

A screening method for one of a therapeutic drug and a preventive drug for hearing loss of the present invention involves the following steps: administering a test substance to a hearing loss model animal; administering a diagnostic composition for an auditory function to the model animal; and examining a staining condition of the diagnostic composition for an auditory function for the hair cell of the model animal. Examples of the hearing loss model animal include an animal auditory impaired with a medicament having auditory toxicity, an animal whose auditory related genes have been knockdown by administration of an antisense nucleic acid, and an animal whose auditory related genes have been knockout with a genetic engineering procedure. As hearing loss genes involved in inherited hearing loss, for example, a gene related to ion transport such as connexin, a gene related to the tectorial membrane construction and the extracellular matrix such as tectorin and a type-XI collagen α2 domain, a gene related to a hair cell stability such as type-VII myosin and type-XV myosin, a gene related to cell differentiation and migration such as factor IV and factor III of POU domain class III, a mitochondrial gene such as A1555G mutation of 12S rRNA, and a COCH gene have been reported for a human, and an animal including a mutation introduced into the genes homologous to the above-mentioned genes is exemplified. In particular, Zebrafish has been already mapped for its genome, and further, has the above-mentioned superiority. Therefore, gene-modified Zebrafish may be suitably used as a hearing loss model animal.

EXAMPLES

Hereinafter, the present invention is described in more detail by way of examples. Those examples are described for the purpose of deeper appreciation of the present invention, and the present invention is not in any way limited to those specific examples. It should be noted that, unless otherwise indicated, "%" means "mass %".

Example 1

<Staining with Probe for Hair Cell>

A staining compound (1) was dissolved in DMSO to prepare a stock solution at a concentration of 1 mg/mL. The stock solution was diluted with distilled water to prepare a hair cell staining solution 1 having a dye concentration of 1 μg/mL. Further, Egg Water was prepared by dissolving artificial seawater SEALIFE (manufactured by Marinetech Co., Ltd.) in distilled water at a concentration of 60 mg/L. Five juveniles (embryos on Day 7 after fertilization) of Zebrafish were placed into any one of wells of a 24-well multiwell plate together with feeding water. The feeding water was discharged and 1 mL of the hair cell staining solution 1 was added. After the whole had been left to stand for 1 hour, the hair cell staining solution 1 in the well was discharged and replaced by 1 mL of fresh Egg Water. In addition, such an operation that Egg Water was discharged and replaced by 1 mL of fresh Egg Water was repeated twice. One of the juveniles was taken out from the well onto a dish, the motion of the juvenile was restricted by addition of methylcellulose, and a fluorescence image was captured with a fluorescence stereomicroscope. MZ16FA manufactured by Leica Microsystems K.K. was used as a stereoscopic microscope.

Examples 2 to 33

The same operation as that in Example 1 was performed except that the staining compound (1) used in Example 1 was changed to each of the staining compounds described in Table 1. An image pickup unit (a digital camera DP72 for a microscope manufactured by Olympus Corporation) of a fluorescence stereomicroscope was remodeled by removing an IR cut filter so as to capture a fluorescence image in a near-infrared wavelength region. In the case of using a staining compound having excitation and fluorescence emission wavelengths in a near-infrared area, the same operation as that in Example 1 was performed with a fluorescence stereomicroscope equipped with the image pickup unit.

Comparative Example 1

The same operation as that in Example 1 was performed except that the staining compound (1) used in Example 1 was changed to 2-(4-(dimethylamino)styryl)-N-ethylpyridinium iodide (DASPEI) and the dye concentration was adjusted to 250 μg/mL.

Comparative Example 2

The same operation as that in Example 1 was performed except that the staining compound (1) used in Example 1 was changed to FM1-43.

Comparative Example 3

The same operation as that in Example 1 was performed except that the staining compound (1) used in Example 1 was changed to indocyanine green (ICG) and the dye concentration was adjusted to 250 μg/mL.

<Evaluation for Fluorescence Intensity>

Based on each of fluorescence observation images in Examples 1 to 33 and Comparative Examples 1 to 3, the fluorescence intensity of a hair cell was visually evaluated (+++: strongly observed, ++: moderately observed, +: weakly observed, and no stained). It should be noted that the excitation wavelength and the fluorescence emission wavelength of the staining compound were determined by measuring an aqueous solution, which had been obtained by diluting 500-fold a 10 mg/mL solution in DMSO with purified water, with a fluorescence spectrophotometer FL 4500 manufactured by Hitachi High-Technologies Corporation.

<Evaluation for Staining Pattern>

By using a fluorescence observation image of each of Examples 1 to 33 and Comparative Examples 1 to 3, the staining properties of the hair cell was visually evaluated (B: a neuromast of big size is mainly stained, S: a neuromast of small size is mainly stained, and BS: both a neuromast of big size and a neuromast of small size are stained).

TABLE 1

| | Staining compound | Excitation wavelength $\lambda ex$ | Fluorescence emission wavelength $\lambda em$ | Fluorescence intensity | Staining pattern |
|---|---|---|---|---|---|
| Example 01 | 1 | 570 | 657 | +++ | S |
| Example 02 | 4 | 401 | 516 | +++ | B |
| Example 03 | 6 | 545 | 636 | +++ | B |
| Example 04 | 8 | 560 | 677 | +++ | B |
| Example 05 | 9 | 520 | 555 | +++ | S |
| Example 06 | 15 | 566 | 611 | +++ | B |
| Example 07 | 16 | 459 | 564 | +++ | S |
| Example 08 | 20 | 650 | 770 | +++ | B |
| Example 09 | 22 | 496 | 569 | +++ | B |
| Example 10 | 25 | 470 | 558 | +++ | S |
| Example 11 | 28 | 429 | 503 | +++ | BS |
| Example 12 | 30 | 561 | 616 | +++ | BS |
| Example 13 | 32 | 545 | 576 | +++ | BS |
| Example 14 | 33 | 478 | 564 | +++ | BS |
| Example 15 | 36 | 516 | 602 | +++ | BS |
| Example 16 | 39 | 563 | 569 | +++ | BS |
| Example 17 | 40 | 344 | 381 | +++ | S |
| Example 18 | 43 | 473 | 564 | +++ | B |
| Example 19 | 45 | 560 | 628 | +++ | B |
| Example 20 | 47 | 354 | 469 | +++ | BS |
| Example 21 | 50 | 571 | 620 | +++ | B |
| Example 22 | 51 | 611 | 720 | +++ | S |
| Example 23 | 53 | 614 | 669 | +++ | BS |
| Example 24 | 54 | 528 | 550 | +++ | B |
| Example 25 | 57 | 570 | 589 | +++ | B |
| Example 26 | 58 | 480 | 509 | +++ | B |
| Example 27 | 60 | 509 | 578 | +++ | B |
| Example 28 | 63 | 490 | 560 | +++ | BS |
| Example 29 | 66 | 770 | 800 | +++ | S |
| Example 30 | 67 | 750 | 780 | +++ | BS |
| Example 31 | 68 | 730 | 760 | +++ | S |
| Example 32 | 69 | 670 | 700 | +++ | BS |
| Example 33 | 70 | 660 | 690 | +++ | BS |
| Comparative Example 1 | DASPEI | 461 | 589 | + | B |
| Comparative Example 2 | FM1-43 | 503 | 627 | +++ | B |
| Comparative Example 3 | ICG | 784 | 811 | No stained | No stained |

Figure 2:
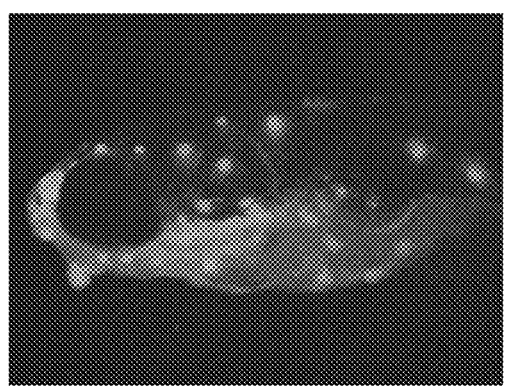
FIG. 2 shows a fluorescence observation image of a Zebrafish neuromast observed in Example 21.
Figure 3:
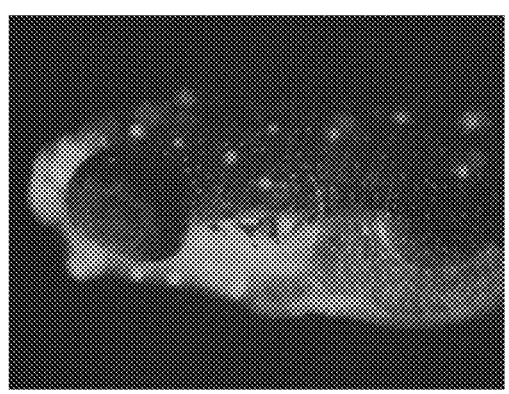
FIG. 3 shows a fluorescence observation image of a Zebrafish neuromast observed in Example 23.

As clear from Table 1, the probe for a hair cell of the present invention is rich in the diversity in the excitation wavelength/fluorescence emission wavelength, and clearly stains a neuromast present in lateral line organs with various patterns and with high fluorescence intensity. Specifically, in a comparison of FIGS. 1 to 3, i.e., an image stained with the probe for a hair cell containing the staining compound (25) in Example 10 (FIG. 1), an image stained with the probe for a hair cell containing the staining compound (50) in Example 21 (FIG. 2), and an image stained with the probe for a hair cell containing the staining compound (53) in Example 23 (FIG. 3), a neuromast containing a hair cell of Zebrafish is stained in all cases, but a large difference is confirmed in patterns of the neuromast to be stained. That is, when the staining compound (25) is used, a portion with a smaller neuromast is selectively stained. Further, when the staining compound (50) is used, a portion with a bigger neuromast is selectively stained. Meanwhile, when the staining compound (53) is used, both a portion with a bigger neuromast and a portion with a smaller neuromast are simultaneously stained.

Example 34

It has been pointed out that an aminoglycoside antibiotic such as gentamicin and an anticancer agent such as cisplatin each have auditory toxicity to a human. Such a chemical substance suspected of having auditory toxicity is exposed to a human model organism, and a change in staining properties of a hair cell is detected by using the probe for a hair cell of the present invention, which enables the auditory toxicity of the chemical substance to be evaluated.

In this example, Zebrafish was selected as the human model organism, and the auditory toxicity of gentamicin was evaluated by using the probe for a hair cell of the present invention as follows. A gentamicin solution having a concentration of 5 µM was exposed to Zebrafish on Day 7 after fertilization for 24 hours. Zebrafish after exposure was washed with distilled water. The same operation as that in Example 1 was performed except that the staining compound (1) used in Example 1 was changed to a staining compound (54).

Example 35

The same operation as that in Example 34 was performed except that the gentamicin solution used in Example 34 was changed to a 5-µM cisplatin solution.

Example 36

The same operation as that in Example 34 was performed except that the gentamicin solution used in Example 34 was changed to a 5-µM taurine solution.

The results of Examples 34 to 36 are shown in Table 2.

TABLE 2

| | Chemical substance to be evaluated | Staining compound | Change in staining intensity | Auditory toxicity |
|---|---|---|---|---|
| Example 34 | Gentamicin | 54 | Weakened | Present |
| Example 35 | Cisplatin | 54 | Weakened | Present |
| Example 36 | Taurine | 54 | No change | Absent |

As a result, changes in the staining intensity and staining pattern confirmed that auditory neuron injury actions of gentamicin and cisplatin can be evaluated, and further, the auditory toxicity of gentamicin and cisplatin is extrapolated from Zebrafish to a human. As clear also from the fact, the probe for a hair cell of the present invention may be used to evaluate the auditory toxicity of a chemical substance.

Example 37

The use of changes in cell staining conditions (staining intensity and fluorescence properties) caused by the probe for a hair cell of the present invention as an index allows the detection and the evaluation of changes in cell conditions (for example, transcriptome, proteome, and metabolome) and functions (for example, viability and membrane potential).

For example, the administration of a specific chemical substance, the depletion of a specific nutrient component, and the administration of an antisense nucleic acid may change the cell conditions and functions. The evaluation of such a change in the staining condition due to artificial intervention to cell conditions and functions enables an effect caused by artificial intervention to be verified.

Meanwhile, an artificial intervention manipulation to cell conditions and functions may also be regarded as the induction of a cell toward a certain kind of disease condition. Therefore, the screening of a substance that restores disease conditions to normal by using a change in cell staining condition with the probe for a hair cell of the present invention as an index allows the selection of a drug candidate substance.

In order to confirm the fact, an experiment for examining the artificial intervention to cell conditions and functions involving the knockdown of a specific gene, and the change in staining properties due to the artificial intervention was performed as follows.

In order to knockdown a specific gene, a mixed solution containing a morpholino antisense oligonucleotide (MO) was prepared. MO was synthesized by using GeneTools, LLC (Philomath, Oreg.). A morpholino antisense oligonucleotide (atgMO) designed so that the translation from a start codon to a protein would be inhibited was dissolved in distilled water to prepare a MO mixed solution having the following composition.

| | |
|---|---|
| atgMO | 10 μg/μL |
| Phenol red | 0.005% |
| EGFP | 50 ng/μL |

A fertilized embryo within 1 hour after fertilization (before a second cleavage period) of Zebrafish was microinjected with the MO mixed solution. A capillary made of glass (inner diameter 0.6 mm) having a sharp extremity obtained by extending and cutting a glass tube with a PC-10 puller (manufactured by Narishige Co., Ltd.) and grinding the cross section with a EG-400 grinder (manufactured by Narishige Co., Ltd.) was used for the microinjection. Feeding water and the fertilized embryo were placed into a 10-cm dish in which 1% agarose had been bedded, and the microinjection was performed under a stereoscopic microscope. During injection, one of a manual injector IM-9A (manufactured by Narishige Co., Ltd.) and an electrical microinjector IM-30 (manufactured by Narishige Co., Ltd.) was connected to the capillary made of glass, to thereby perform infusion with pressure. The infusion amount of MO was set to 1 to 10 ng per fertilized embryo.

Because the MO mixed solution is supplemented with a dye (0.005% phenol red), the success or failure of the infusion of the MO mixed solution may be confirmed with the naked eye. Further, because the MO mixed solution is supplemented with a fluorescent protein expression vector (EGFP), on Day 3 after infusion, the success or failure of the microinjection can be confirmed after the fertilized embryo has hatched (a sample in which a signal derived from the fluorescent protein was observed also retains MO in Zebrafish).

Juveniles (embryos on Day 7 after fertilization) of Zebrafish were stained in the same manner as that in Example 1, and a change in staining condition of the hair cell was measured.

The compound (54) was selected as the probe for a hair cell and compared with FM1-43. Further, SLC25A12 and TRPC2 were selected as target genes. The staining intensity of a juvenile neuromast having unknockdown genes was used as a control, and compared with the staining intensity of a juvenile neuromast in which each of the target genes has been knockdown by representing a fluorescence image obtained with a stereoscopic microscope in numerical values.

Table 3 shows the change in staining intensity of the neuromast due to the knockdown (KD) of each of the target genes.

TABLE 3

| Target gene | Compound | Number of sample (N_KD) | Number of sample (N_control) | Ratio of staining intensity (KD/control) | p value |
|---|---|---|---|---|---|
| SLC25A12 | (54) | 27 | 26 | 2.06 | 0.009 |
| SLC25A12 | FM1-43 | 16 | 18 | 1.36 | 0.027 |
| TRPC2 | (54) | 20 | 21 | 2.18 | 0.0003 |
| TRPC2 | FM1-43 | 11 | 12 | 1.35 | 0.024 |

The staining properties with the compound (54) were significantly increased about 2-fold by the knockdown of the SLC25A12 and TRPC2 genes, respectively. Meanwhile, the staining properties with FM1-43 were also significantly increased by the knockdown each of the SLC25A12 and TRPC2 genes, but the ratio was about 30%, which was smaller than the compound (54).

The fact indicates that the probe for a hair cell of the present invention may detect more perceptively a change in staining properties due to artificial intervention to cell functions.

Further, because a chemical structure of compound (54) is different from a chemical structure of FM1-43, the compound (54) and FM1-43 may be different in the staining mechanism of the hair cell.

Example 38

The probe for a hair cell of the present invention includes an agent whose staining intensity is higher compared with that with a conventionally known staining agent such as FM1-43. In order to confirm the fact, an experiment for examining a change in staining properties by changing the concentration of the staining agent was performed as follows.

The compounds (43), (54), and (65) were selected as probes for a hair cell, and compared with FM1-43. Three kinds of staining solutions containing those staining agents were prepared at concentrations of 10 ng/mL, 30 ng/mL, and 100 ng/mL. Juveniles of (embryos on Day 7 after fertilization) of Zebrafish were stained in the same manner as that in Example 1. When a fluorescence image is acquired with a fluorescence stereomicroscope, the fluorescence intensity per unit intake time (intensity/msec) was calculated by changing an intake time (exposure time) and dividing the fluorescence intensity (Relative Fluorescence Unit, RFU) of a neuromast of the obtained fluorescence image by the intake time.

Figure 4:
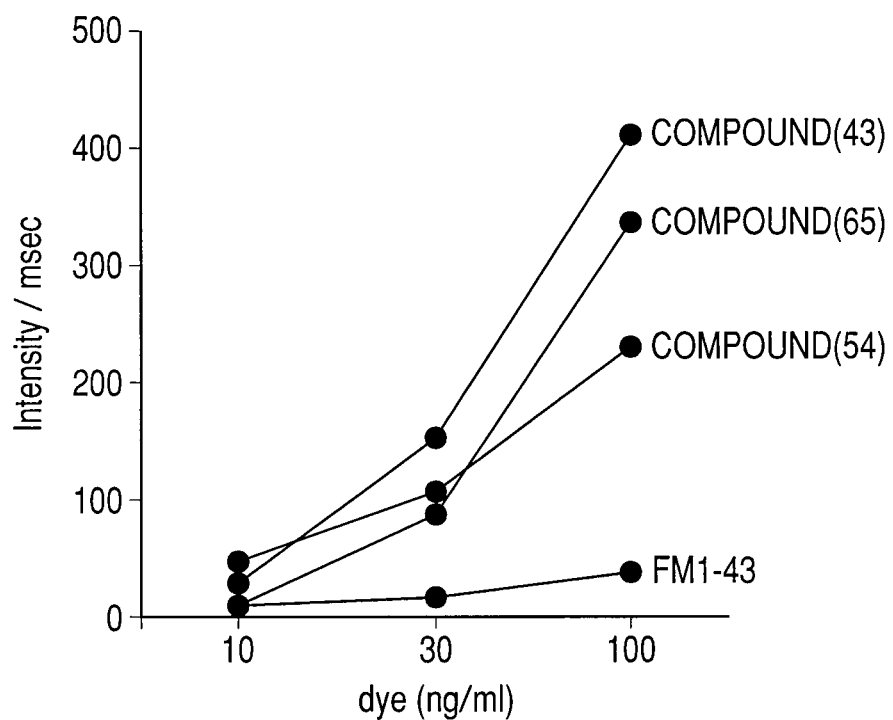
FIG. 4 illustrates a comparison (intensity/msec) in fluorescence intensity (relative fluorescence unit, RFU) measured in Example 38.

FIG. 4 shows the results. The results confirmed that the staining intensity of the hair cell with the compounds (43), (54), and (65) were higher compared with the staining intensity with FM1-43.

The probe for a hair cell having high staining intensity of the present invention may be used at lower concentrations. Also, a clear staining image with small background noise may be obtained. In addition, the wide dynamic range of a staining signal allows the more detailed analysis of the hair cell for its physiological conditions.

<Industrial Applicability>

Sensorineural hearing loss resulting from the induction of cell death of an inner ear hair cell is hearing loss which widely develops in the range of newborns to senior adults owing to congenital and acquired causes, and there are many unclear points about detailed pathogenesis. Therefore, there is a strong demand for the establishment of an effective treatment method.

The probe for a hair cell of the present invention has a variety of chemical structures, is rich in the diversity in the excitation wavelength/fluorescence emission wavelength, and can clearly stain a neuromast present in lateral line organs of Zebrafish with various patterns and with high fluorescence intensity. The difference in the staining pattern probably reflects that each of the probes for a hair cell stains the hair cell by a different mechanism, which allows the identification of various conditions of the hair cell.

In the probe for a hair cell of the present invention, the staining condition may greatly change depending on cell conditions and functions, and hence, an auditory function can be evaluated from various angles.

Based on the evaluation for an auditory function using the probe for a hair cell of the present invention, an effective treatment method, therapeutic drug, and preventive drug for sensorineural hearing loss may be developed.

Further, the screening of one of a therapeutic drug and a preventive drug for hearing loss is accelerated by use of Zebrafish, which leads to a cost reduction. Still further, one of a therapeutic drug and a preventive drug for hearing loss can be easily evaluated.

Further, the probe for a hair cell may be used as an index during screening for evaluating the auditory toxicity of a chemical substance.

In addition, the analysis of a change in staining condition due to artificial intervention to cell conditions and functions allows the verification of an effect of the artificial intervention. Thus, the probe for a hair cell may become an effective tool for a bioscience research.

While the present invention has been described with reference to exemplary embodiments, it is to be understood that the invention is not particularly limited to the disclosed exemplary embodiments. The scope of the following claims is to be accorded the broadest interpretation so as to encompass all such modifications and equivalent structures and functions.

This application claims the benefit of Japanese Patent Application No. 2008-330979, filed on Dec. 25, 2008, which is hereby incorporated by reference herein in its entirety.

What is claimed is:

1. A labelling method for a hair cell comprising administering to a biological specimen a probe for a hair cell which contains as an active agent a staining compound represented by the general formula (I)

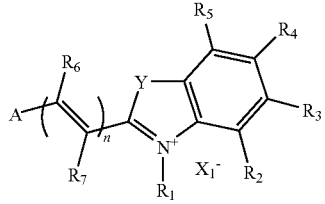
(I)

wherein:
$R_1$ represents a hydrogen atom, an alkyl group, or an aryl group;

$R_2$ to $R_5$ each independently represent a hydrogen atom, an alkyl group, an aryl group, an alkoxy group, a carboxylic acid group, a sulfonic acid group, a heterocyclic group, an amino group, or a halogen atom, and $R_2$ and $R_3$, $R_3$ and $R_4$, or $R_4$ and $R_5$ are optionally bonded to each other to form a ring;

$R_6$ represents a hydrogen atom or an alkyl group;

$R_7$ represents a hydrogen atom, an alkyl group, a carboxylic acid group, or a cyano group;

$X_1^-$ represents an anionic group;

Y represents a sulfur atom, an oxygen atom, —N($R_8$)—, or —C($R_9$)($R_{10}$)—, wherein $R_8$ to $R_{10}$ each independently represent a hydrogen atom, an alkyl group, or an aryl group, and $R_9$ and $R_{10}$ are optionally bonded to each other to form a ring;

n represents an integer of 1 to 3; and

A represents the general formula (IV)

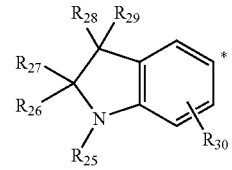
(IV)

wherein:
$R_{25}$ represents a hydrogen atom, an alkyl group, an aralkyl group, an alkenyl group, an aryl group, a heterocyclic group, or an acyl group;

$R_{26}$ to $R_{29}$ each independently represent a hydrogen atom, an alkyl group, an aryl group, a carboxylic acid group, a carboxylic acid ester group, or an acyl group, and $R_{26}$ and $R_{28}$ are bonded to each other to form a cyclopentane ring; and $R_{30}$ represents a hydrogen atom, an alkyl group, an alkoxy group, or a halogen atom.

2. The labelling method for a hair cell according to claim 1, wherein the compounds represented by the general formula (I) comprise at least one of a carboxylic acid group or a sulfonic acid group.

3. An imaging method for a hair cell, comprising:
administering to a biological specimen a probe for a hair cell; and
observing fluorescence derived from the probe for a hair cell by irradiating the biological specimen with excitation light;
wherein the probe for a hair cell contains as an active agent a staining compound represented by the general formula (I)

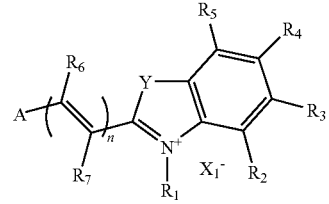
(I)

wherein:
$R_1$ represents a hydrogen atom, an alkyl group, or an aryl group;

$R_2$ to $R_5$ each independently represent a hydrogen atom, an alkyl group, an aryl group, an alkoxy group, a carboxylic acid group, a sulfonic acid group, a heterocyclic group, an amino group, or a halogen atom, and $R_2$ and $R_3$, $R_3$ and $R_4$, or $R_4$ and $R_5$ are optionally bonded to each other to form a ring;

$R_6$ represents a hydrogen atom or an alkyl group;

$R_7$ represents a hydrogen atom, an alkyl group, a carboxylic acid group, or a cyano group;

$X_1^-$ represents an anionic group;

Y represents a sulfur atom, an oxygen atom, —N($R_8$)—, or —C($R_9$)($R_{10}$)—, wherein $R_8$ to $R_{10}$ each independently represent a hydrogen atom, an alkyl group, or an aryl group, and $R_9$ and $R_{10}$ are optionally bonded to each other to form a ring;

n represents an integer of 1 to 3; and

A represents the general formula (IV)

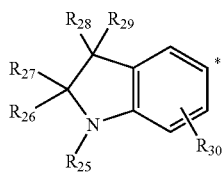

(IV)

wherein:

$R_{25}$ represents a hydrogen atom, an alkyl group, an aralkyl group, an alkenyl group, an aryl group, a heterocyclic group, or an acyl group;

$R_{26}$ to $R_{29}$ each independently represent a hydrogen atom, an alkyl group, an aryl group, a carboxylic acid group, a carboxylic acid ester group, or an acyl group, and $R_{26}$ and $R_{28}$ are bonded to each other to form a cyclopentane ring; and $R_{30}$ represents a hydrogen atom, an alkyl group, an alkoxy group, or a halogen atom.

4. An evaluation method for auditory toxicity of a chemical substance, comprising:

administering the chemical substance to an organism;

administering to the organism a probe for a hair cell; and observing fluorescence derived from the probe for a hair cell by irradiating the organism with excitation light;

wherein the probe for a hair cell contains as an active agent a staining compound represented by the general formula (I)

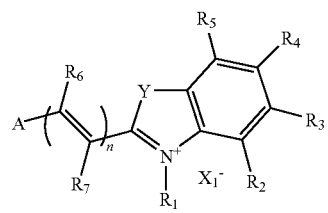

(I)

wherein:

$R_1$ represents a hydrogen atom, an alkyl group, or an aryl group;

$R_2$ to $R_5$ each independently represent a hydrogen atom, an alkyl group, an aryl group, an alkoxy group, a carboxylic acid group, a sulfonic acid group, a heterocyclic group, an amino group, or a halogen atom, and $R_2$ and $R_3$, $R_3$ and $R_4$, or $R_4$ and $R_5$ are optionally bonded to each other to form a ring;

$R_6$ represents a hydrogen atom or an alkyl group;

$R_7$ represents a hydrogen atom, an alkyl group, a carboxylic acid group, or a cyano group;

$X_1^-$ represents an anionic group;

Y represents a sulfur atom, an oxygen atom, —N($R_8$)—, or —C($R_9$)($R_{10}$)—, wherein $R_8$ to $R_{10}$ each independently represent a hydrogen atom, an alkyl group, or an aryl group, and $R_9$ and $R_{10}$ are optionally bonded to each other to form a ring;

n represents an integer of 1 to 3; and

A represents the general formula (IV)

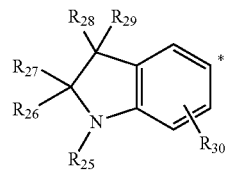

(IV)

wherein:

$R_{25}$ represents a hydrogen atom, an alkyl group, an aralkyl group, an alkenyl group, an aryl group, a heterocyclic group, or an acyl group;

$R_{26}$ to $R_{29}$ each independently represent a hydrogen atom, an alkyl group, an aryl group, a carboxylic acid group, a carboxylic acid ester group, or an acyl group, and $R_{26}$ and $R_{28}$ are bonded to each other to form a cyclopentane ring; and $R_{30}$ represents a hydrogen atom, an alkyl group, an alkoxy group, or a halogen atom.

5. The evaluation method for auditory toxicity of a chemical substance according to claim 4, wherein the organism comprises Zebrafish.

6. A screening method for a therapeutic drug for hearing loss, comprising:

administering a test substance to a hearing loss model animal;

administering a diagnostic composition for an auditory function to the hearing loss model animal; and examining a staining condition of the diagnostic composition for an auditory function for a hair cell of the hearing loss model animal;

wherein the diagnostic composition for an auditory function comprises a probe for a hair cell, and wherein the probe for a hair cell contains as an active agent a staining compound represented by the general formula (I)

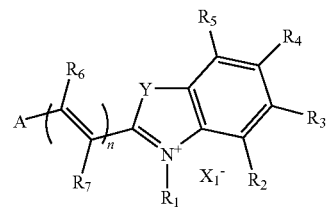

(I)

wherein:

$R_1$ represents a hydrogen atom, an alkyl group, or an aryl group;

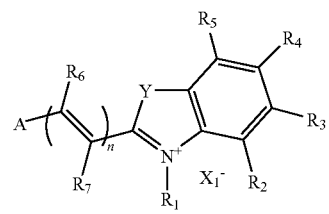

(I)

wherein:
R₁ represents a hydrogen atom, an alkyl group, or an aryl group;
R₂ to R₅ each independently represent a hydrogen atom, an alkyl group, an aryl group, an alkoxy group, a carboxylic acid group, a sulfonic acid group, a heterocyclic group, an amino group, or a halogen atom, and R₂ and R₃, R₃ and R₄, or R₄ and R₅ are optionally bonded to each other to form a ring;
R₆ represents a hydrogen atom or an alkyl group;
R₇ represents a hydrogen atom, an alkyl group, a carboxylic acid group, or a cyano group;
X₁⁻ represents an anionic group;
Y represents a sulfur atom, an oxygen atom, —N(R₈)—, or —C(R₉)(R₁₀)—, wherein R₈ to R₁₀ each independently represent a hydrogen atom, an alkyl group, or an aryl group, and R₉ and R₁₀ are optionally bonded to each other to form a ring;
n represents an integer of 1 to 3; and
A represents the general formula (IV)

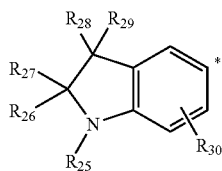

(IV)

wherein:
R₂₅ represents a hydrogen atom, an alkyl group, an aralkyl group, an alkenyl group, an aryl group, a heterocyclic group, or an acyl group;
R₂₆ to R₂₉ each independently represent a hydrogen atom, an alkyl group, an aryl group, a carboxylic acid group, a carboxylic acid ester group, or an acyl group, and R₂₆ and R₂₈ are bonded to each other to form a cyclopentane ring; and
R₃₀ represents a hydrogen atom, an alkyl group, an alkoxy group, or a halogen atom.

7. The screening method according to claim 6, wherein the hearing loss model animal comprises Zebrafish.

8. An evaluation method for a therapeutic drug for hearing loss, comprising:
administering a test substance to a hearing loss model animal;
administering a diagnostic composition for an auditory function to the hearing loss model animal; and
examining a staining condition of the diagnostic composition for an auditory function for a hair cell of the hearing loss model animal;
wherein the diagnostic composition for an auditory function comprises a probe for a hair cell, and
wherein the probe for a hair cell contains as an active agent a staining compound represented by the general formula (I)

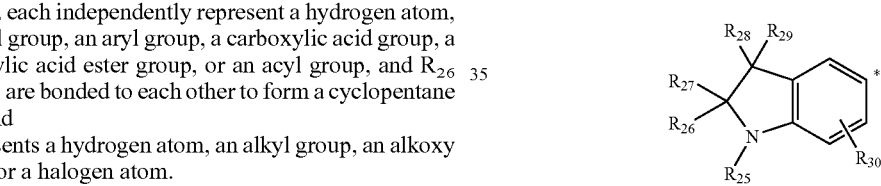

(I)

wherein:
R₁ represents a hydrogen atom, an alkyl group, or an aryl group;
R₂ to R₅ each independently represent a hydrogen atom, an alkyl group, an aryl group, an alkoxy group, a carboxylic acid group, a sulfonic acid group, a heterocyclic group, an amino group, or a halogen atom, and R₂ and R₃, R₃ and R₄, or R₄ and R₅ are optionally bonded to each other to form a ring;
R₆ represents a hydrogen atom or an alkyl group;
R₇ represents a hydrogen atom, an alkyl group, a carboxylic acid group, or a cyano group;
X₁⁻ represents an anionic group;
Y represents a sulfur atom, an oxygen atom, —N(R₈)—, or —C(R₉)(R₁₀)—, wherein R₈ to R₁₀ each independently represent a hydrogen atom, an alkyl group, or an aryl group, and R₉ and R₁₀ are optionally bonded to each other to form a ring;
n represents an integer of 1 to 3; and
A represents the general formula (IV)

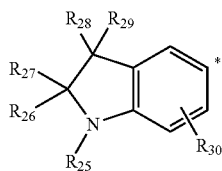

(IV)

wherein:
R₂₅ represents a hydrogen atom, an alkyl group, an aralkyl group, an alkenyl group, an aryl group, a heterocyclic group, or an acyl group;
R₂₆ to R₂₉ each independently represent a hydrogen atom, an alkyl group, an aryl group, a carboxylic acid group, a carboxylic acid ester group, or an acyl group, and R₂₆ and R₂₈ are bonded to each other to form a cyclopentane ring; and
R₃₀ represents a hydrogen atom, an alkyl group, an alkoxy group, or a halogen atom.

9. The evaluation method according to claim 6, wherein the hearing loss model animal comprises Zebrafish.

* * * * *